(12) United States Patent
Prieve et al.

(10) Patent No.: US 6,269,680 B1
(45) Date of Patent: *Aug. 7, 2001

(54) METHOD AND APPARATUS FOR MEASURING THE CONCENTRATION OF HYDROGEN PEROXIDE VAPOR

(75) Inventors: John F. Prieve, Seattle, WA (US); Paul Taylor Jacobs, Trabuco Canyon; Szu-Min Lin, Laguna Hills, both of CA (US); Richard B. Timmons, Arlington, TX (US)

(73) Assignee: Ethicon, Inc., New Brunswick, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/337,727

(22) Filed: Jun. 21, 1999

Related U.S. Application Data

(63) Continuation of application No. 08/970,925, filed on Nov. 14, 1997, now abandoned.

(51) Int. Cl.[7] .................................................. G01N 21/35
(52) U.S. Cl. .......................... 73/23.21; 73/23.2; 250/373; 422/28; 436/135
(58) Field of Search .................................... 250/373, 372; 436/135; 73/24.02, 24.06, 23.2, 23.21; 422/28; 356/437

(56) References Cited

U.S. PATENT DOCUMENTS 3,498,720 * 3/1970 Kohlhaas et al. ..................... 250/372
4,419,452 12/1983 Imai et al. .

(List continued on next page.)

FOREIGN PATENT DOCUMENTS

| 0916937A2 | * 5/1999 | (EP) . |
| 62 063836 A | 3/1987 | (JP) . |
| 62 079331 A | 4/1987 | (JP) . |
| PCT/US96/09625 | 6/1996 | (WO) . |

OTHER PUBLICATIONS

Optical Methods of Gas Analysis—(confidential presentation to Assignee) Random Technologies Proprietary Information Feb. 10, 1995.

(List continued on next page.)

Primary Examiner—Hezron Williams
Assistant Examiner—Michael Cygan
(74) Attorney, Agent, or Firm—Knobbe, Martens, Olson & Bear, LLP.

(57) ABSTRACT

An improved apparatus and method for measuring the concentration of hydrogen peroxide vapor or gas in a sterilization chamber. The hydrogen peroxide is measured spectrophotometrically in the ultraviolet region between 200 and 400 nm. Because water vapor does not absorb in the ultraviolet region, it does not interfere with the determination of the concentration of the hydrogen peroxide vapor. Although organic compounds have absorbances in the ultraviolet region, the organic compounds are removed by evacuating the sterilization chamber to low levels before doing the hydrogen peroxide determination. The ultraviolet light source is either a low pressure mercury vapor lamp with an emission at 254 nm or a deuterium lamp with an optical filter selective of 206 nm light. A movable gas cell can be used to measure the hydrogen peroxide concentration at various areas in the sterilization chamber. The measurement system can be combined with a feedback loop to control the concentration of hydrogen peroxide in the sterilization chamber.

21 Claims, 14 Drawing Sheets

U.S. PATENT DOCUMENTS

| | | | | |
|---|---|---|---|---|
| 4,518,895 | * | 5/1985 | Lehman | 315/117 |
| 4,601,582 | * | 7/1986 | Casey, Jr. | 356/414 |
| 4,643,876 | * | 2/1987 | Jacobs et al. | 422/28 |
| 4,843,867 | | 7/1989 | Cummings | 73/23 |
| 4,956,145 | | 9/1990 | Cummings et al. . | |
| 5,081,044 | | 1/1992 | Buckler et al. . | |
| 5,139,956 | | 8/1992 | Schick et al. . | |
| 5,152,968 | * | 10/1992 | Foti et al. | 422/304 |
| 5,170,057 | * | 12/1992 | Danielson | 250/373 |
| 5,244,629 | * | 9/1993 | Caputo et al. | 422/22 |
| 5,378,436 | | 1/1995 | Endoh et al. . | |
| 5,445,792 | | 8/1995 | Rickloff et al. . | |
| 5,600,142 | | 2/1997 | Van Den Berg et al. | 250/339.13 |
| 5,608,156 | | 3/1997 | Ando et al. | 73/31.06 |
| 5,788,925 | * | 8/1998 | Pai et al. | 73/865.9 |
| 5,936,250 | * | 8/1999 | Baliga et al. | 250/373 |
| 5,955,025 | * | 9/1999 | Barrett | 422/28 |
| 6,030,579 | * | 2/2000 | Addy et al. | 422/28 |
| 6,039,922 | * | 3/2000 | Swank et al. | 422/28 |

OTHER PUBLICATIONS

Theoretical Study on the Quasi–Bound State and UV Spectrum of H2O2 with Inclusion of the Vibrational Structure Kouichi Takeshita, P.K. Mukherjee/Chemical Physics 182 (1994) pp. 195–201.

Ultraviolet Absorption Cross Sections of Hydrogen Peroxide C.L. Lin, N.K. Rohatgi, and W. B. DeMore/Geophysical Research Letters vol. 5 No. 2/Feb. 1978.

Oh Yield From Photodissociation of H2O2 at 106–193nm Masako Suto and L.C. Lee/Chemical Physics Letters/vol. 98 No. 2—Jun. 17, 1983 pp. 152–156.

Ultraviolet Absorption Spectrum of Hydrogen Peroxide Vapor Luisa T. Molina, Stanley D. Schinke and Mario J. Molina/ Geophysical Research Letters vol. 4 No. 12/ Dec. 1977.

* cited by examiner

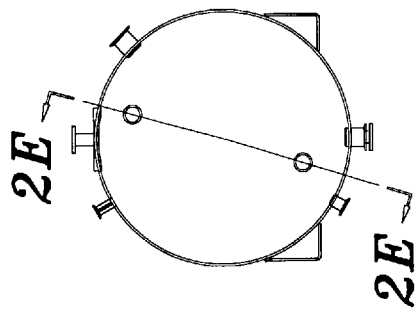
FIG.2D SECTION A-A
FIG.2E SECTION B-B
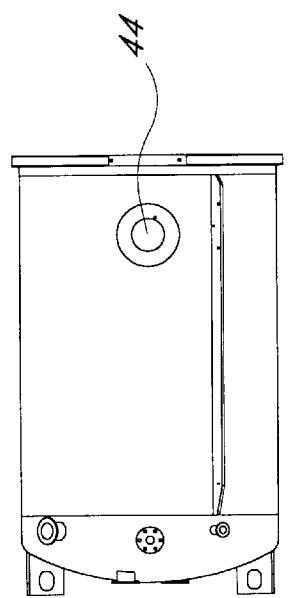
FIG.2B
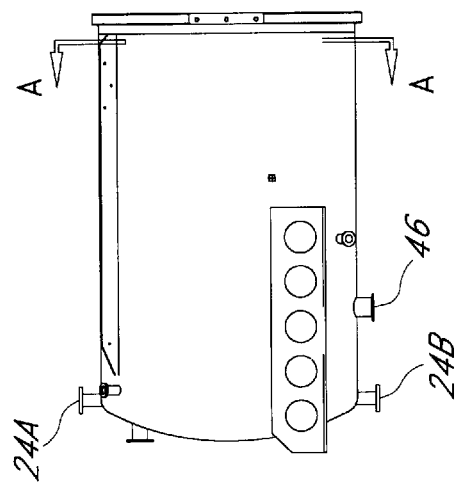
FIG.2A
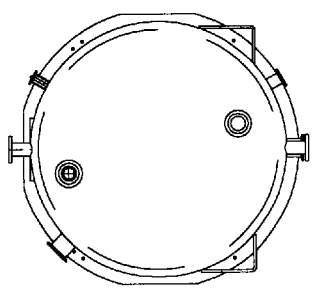
FIG.2C

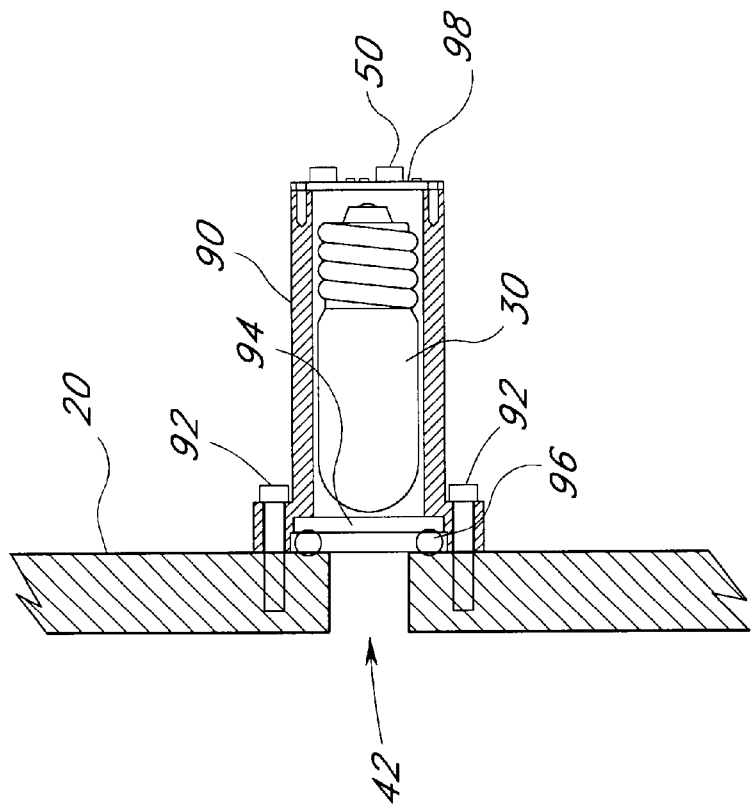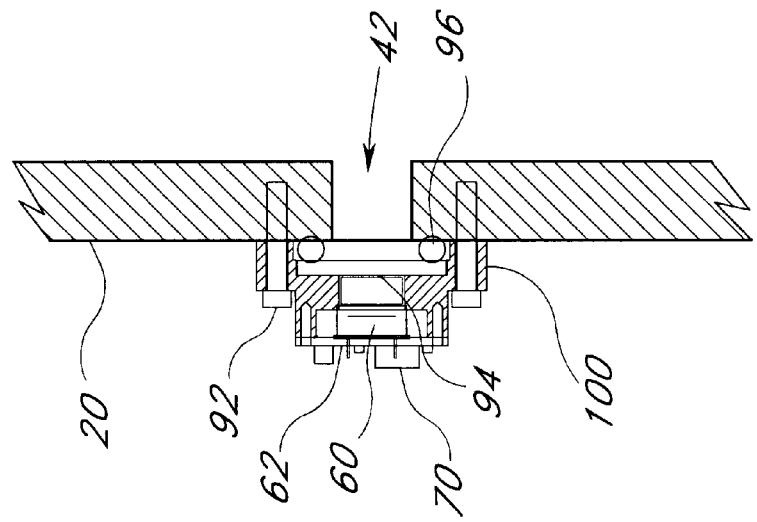
FIG. 7

METHOD AND APPARATUS FOR MEASURING THE CONCENTRATION OF HYDROGEN PEROXIDE VAPOR

This application is a continuation of application Ser. No. 08/970,925, filed on Nov. 14, 1997 abandoned.

FIELD OF THE INVENTION

This invention relates to an apparatus and a method for measuring the concentration of hydrogen peroxide vapor or gas.

BACKGROUND OF THE INVENTION

Sterilization is used in a broad range of industrial and medical applications. Sterilization is the complete destruction or irreversible inactivation of all microorganisms. There are many methods for sterilizing, including heat and chemical methods. Heat sterilization is normally done using steam. Some equipment cannot withstand either the heat or the moisture from steam treatment. As a result, chemical sterilization is now commonly used.

Chemical sterilization can be done using alcohols, aldehydes such as formaldehyde, phenols, ozone, ethylene oxide, or hydrogen peroxide. Chemical sterilization does not normally require the use of heat. The method is thus commonly called cold sterilization. Hydrogen peroxide is commonly used today for chemical sterilization.

Use of low concentrations of hydrogen peroxide for chemical sterilization has many advantages. It is easy to handle, can be stored for long periods of time, is noncorrosive, and mixes readily with water. When it decomposes, it forms water and oxygen, nontoxic materials. However, there are problems with using hydrogen peroxide for sterilization. In order to be effective, it must be maintained at a specified concentration. It is therefore normally desirable to maintain as high a concentration as practical during sterilization. Furthermore, hydrogen peroxide will react with some surfaces undergoing sterilization and will also permeate into and through some plastic materials. All of these factors can reduce the concentration of the hydrogen peroxide to levels that make it ineffective at sterilization.

Hydrogen peroxide vapor can condense onto the walls of the sterilization chamber or onto equipment in the chamber. The condensed hydrogen peroxide can potentially degrade or harm the chamber or the equipment.

It is therefore important to be able to determine the concentration of hydrogen peroxide vapor in the sterilization chamber so that enough hydrogen peroxide vapor is present to be effective, but not so much that the hydrogen peroxide vapor damage the equipment.

The concentration of hydrogen peroxide vapor throughout the chamber can vary, because he equipment placed in the chamber can restrict diffusion of sterilant vapor. There may therefore be areas of the chamber which are exposed to higher or lower concentrations of hydrogen peroxide due to these flow restrictions. It is therefore desirable to be able to determine the concentration of hydrogen peroxide in different areas of the sterilization chamber in order to measure the variation in concentration through the sterilization chamber.

There are methods for determining levels of hydrogen peroxide in sterilization chambers. Ando et al. (U.S. Pat. No. 5,608,156) disclose using a semiconductor gas sensor as a means of measuring vapor phase hydrogen peroxide concentrations. The reaction time of the sensor is several tens of seconds, however, and the relation between the sensor output and the concentration of the hydrogen peroxide vapor varies with changes in pressure. Most hydrogen peroxide vapor sterilization procedures involve several treatment steps, usually including at least one step with vacuum. The response of the sensor to hydrogen peroxide through the treatment steps will therefore change, depending on the pressure used in each treatment step.

Cummings (U.S. Pat. No. 4,843,867) discloses a system for determining the concentration of hydrogen peroxide vapor in-situ by simultaneous measurements of two separate properties such as dew point and relative humidity. A microprocessor is then used to fit the two measurements into a model to calculate the hydrogen peroxide concentration. The method uses an indirect approximation based on a number of empirical assumptions, and the accuracy will vary depending on how closely the conditions in the sterilization chamber resemble those used to develop the model.

Van Den Berg et al. (U.S. Pat. No. 5,600,142) disclose a method using near infrared (NIR) spectroscopy to detect hydrogen peroxide vapor. Hydrogen peroxide has an absorption peak at about 1420 nm (nanometers) which can be used to determine its concentration. Water also absorbs in this region, however, and it therefore interferes with the determination of the concentration of hydrogen peroxide. Water is always present when hydrogen peroxide is present, because it is a decomposition product. In order to correct for the interference from water vapor, the water vapor concentration is determined by doing a measurement at remote wavelengths where hydrogen peroxide is transparent. This measured water vapor concentration is used to correct the absorbance at 1420 nm for the contribution due to water. Organic molecules also absorb in this same region, however, and the correction factor for organic molecules depends on the organic compounds which are present. The correction for organic vapors is therefore somewhat subjective, because one does not normally know what organics are present.

The NIR method requires doing measurements at two different wavelengths and making corrections for the presence of water vapor, organics, or both. The electronic equipment for doing these corrections is complex and expensive, and the correction for the presence of organic compounds is subjective.

There is a need for a method of determining the concentration of hydrogen peroxide vapor or gas that is not dependent on correcting for the presence of water vapor and organic molecules. There is also a need for a method of measuring hydrogen peroxide that does not require the use of expensive electronics, such as those which do measurements at two different wavelengths and apply complex correction factors.

SUMMARY OF THE INVENTION

In the method of determining the concentration of hydrogen peroxide vapor or gas according to the method of the present invention, the sterilization chamber is evacuated to a pressure of about 500 millitorr to remove organic compounds which would interfere with the determination. Hydrogen peroxide is introduced into the sterilization chamber. These two steps can be done in either order. The absorbance of the hydrogen peroxide vapor or gas is then determined at a wavelength between 200 and 400 nanometers, the ultraviolet region. Hydrogen peroxide absorbs in this region, but water vapor does not. By doing the absorbance measurement of hydrogen peroxide vapor in the ultraviolet region, the interference from water vapor is eliminated. The concentration of hydrogen peroxide vapor or gas in the sterilization chamber is determined from the absorbance in the ultraviolet region. Based on the measured concentration of hydrogen peroxide, the concentration may optionally be adjusted by adding more hydrogen peroxide so that the concentration is high enough to be effective at sterilization but not so high as to condense onto equipment in the sterilization chamber.

In accordance with another aspect of this invention, the concentration of hydrogen peroxide as measured by the method of the invention can be compared with a desired set point concentration. Additional hydrogen peroxide can be incrementally added with a controller to increase the concentration of hydrogen peroxide until the set point concentration is reached. In this manner, the method of the invention can be used for feedback control of the concentration of hydrogen peroxide vapor or gas.

Preferably, the absorbance measurement is done at a wavelength of 254 nanometers. Advantageously, the absorbance at this wavelength is measured using a mercury lamp. Even more advantageously, the mercury lamp is current regulated to provide stability of the mercury lamp.

In accordance with another aspect of this invention, the absorbance of the hydrogen peroxide vapor or gas is measured at a wavelength of 206 nanometers. Advantageously, the absorbance at this wavelength is measured using a deuterium lamp.

In accord with one aspect of this invention, the concentration of hydrogen peroxide vapor or gas is determined from the absorbance using Beer's law. As another aspect of this invention, the concentration of hydrogen peroxide vapor or gas is determined by comparing the absorbance with a calibration curve of absorbance versus the concentration of hydrogen peroxide vapor or gas.

In accordance with another aspect of this invention, the apparatus for measuring the concentration of hydrogen peroxide vapor or gas comprises an ultraviolet light source generating light in the range of 200 to 400 nanometers, an optical radiation detector capable of detecting the ultraviolet light, an optical path between the ultraviolet light source and the optical radiation detector, and a source of hydrogen peroxide vapor or gas.

Preferably, the apparatus also contains a vacuum pump to evacuate the optical path to a pressure of about 500 millitorr so that organic compounds which can interfere with the determination can be removed.

According to another aspect of this invention, the source of hydrogen peroxide vapor or gas contains a heater to increase the rate of volatilization of the hydrogen peroxide. As another aspect, the source of hydrogen peroxide contains a ultrasonic source as an alternative way to increase the rate of volatilization of the hydrogen peroxide.

In accordance with another aspect of the invention, the apparatus also contains a controller for maintaining a desired hydrogen peroxide concentration, the set point concentration, through feedback control.

In accord with one aspect of this invention, the ultraviolet light source is a mercury lamp. In another aspect of this invention, the ultraviolet light source is a deuterium lamp. Advantageously, there is an optical filter selective of 206 nanometer light located between the deuterium lamp and the optical radiation detector.

In accord with another aspect of this invention, the apparatus includes a movable gas cell, which can be moved around the sterilization chamber so that measurements of the concentration of hydrogen peroxide can be done at various locations inside the sterilization chamber. The ends of the movable gas cell are connected to the ultraviolet lamp and the detector with optical fibers.

The method and apparatus of the invention thus use an ultraviolet light source to determine the concentration of hydrogen peroxide vapor or gas in a sterilization chamber. Use of ultraviolet light eliminates the interference of water vapor with the determination and allows for use of simple and inexpensive electronics in the conversion of the ultraviolet absorbance to the concentration of hydrogen peroxide gas or vapor. Evacuating the chamber eliminates the interference of organic compounds. After the concentration of hydrogen peroxide vapor or gas has been determined with the method and apparatus of this invention, the concentration can be adjusted upward to optimize the sterilization of the equipment without condensing hydrogen peroxide onto the equipment or walls of the sterilization chamber with resulting potential damage.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

FIG. 2 is a series of drawings showing different views of a form of a sterilization chamber in which the method of the present invention can be practiced;

FIG. 7 is a sectional view of a preferred method of attaching the optical equipment to flat walls of the sterilization chamber;

DETAILED DESCRIPTION OF THE PREFERRED EMBODIMENT

The present invention involves an apparatus and a method for measuring gas phase concentrations of hydrogen peroxide in the presence of water vapor. The apparatus and method are intended for use in vapor sterilization procedures using hydrogen peroxide. Because hydrogen peroxide decomposes to oxygen and water, the gaseous samples to be analyzed always contain a mixture of hydrogen peroxide and water. In the method of the present invention, gas phase hydrogen peroxide is measured spectrophotometrically using an ultraviolet light source rather than the near infrared (NIR) source of the previous invention. When the spectroscopic measurement is done in the NIR by the method of the previous invention, absorbance measurements must be done at two different wavelengths, because both water and hydrogen peroxide absorb in the NIR The concentration of water is determined at a wavelength at which it absorbs and the hydrogen peroxide does not. The interference of the water vapor with the hydrogen peroxide absorbance at the other wavelength is subtracted to obtain the absorbance due to hydrogen peroxide alone. Under the method of the present invention, an ultraviolet light source is used. There is no need to do the determination at two different wavelengths, determine water separately, and correct the hydrogen peroxide absorbance for the water interference, because water does not absorb in the ultraviolet region of the spectrum. The instrumentation, associated electronics, and the analysis procedure are therefore all simpler than in the previous invention.

However, many organic molecules absorb strongly in the ultraviolet region. Organic vapors are likely to be present in the samples due to outgassing of equipment in the sterilization chamber, the presence of organic solvents, etc. The interference from organic molecules is difficult to subtract from the absorbance due to hydrogen peroxide, because each organic molecule has its own absorption spectrum and intensities. Without knowing the identity of the organic species, one does not know what correction factor to use to subtract the absorbance due to the organic compounds. In the present invention, these interfering absorption peaks in the ultraviolet region due to species such as organic molecules are removed hy evacuating the sterilization chamber to a low level, far lower than in the previous invention. This improvement eliminates the necessity to subtract the absorption intensities of these interfering species from the absorption due to hydrogen peroxide. A series of other improvements in the apparatus, electronics, and procedures enhance the stability of the ultraviolet light source and detector and the sensitivity of the method. The preferred embodiment uses a combination of these improvements to obtain the maximum benefit of the present invention.

Measurement Device

Figure 1:
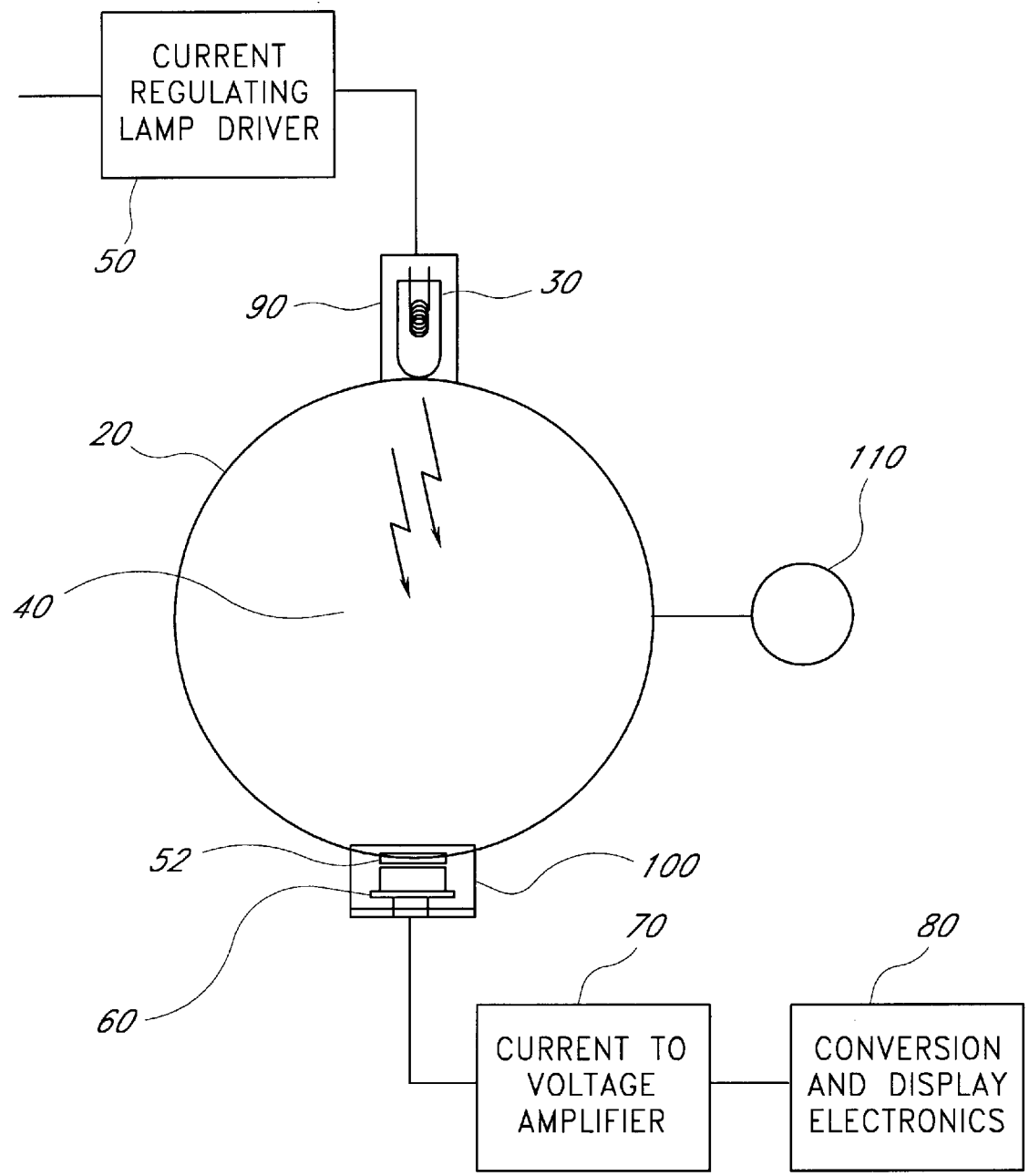
FIG. 1 is a schematic drawing of the overall system of the present invention for measuring the concentration of hydrogen peroxide vapor.
Figure 3D:
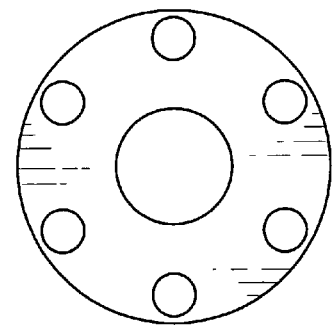
FIG. 3 is a perspective drawing and several views of an aluminum flange suitable for forming an optical path on curved walls of the sterilization chamber.
Figure 3C:
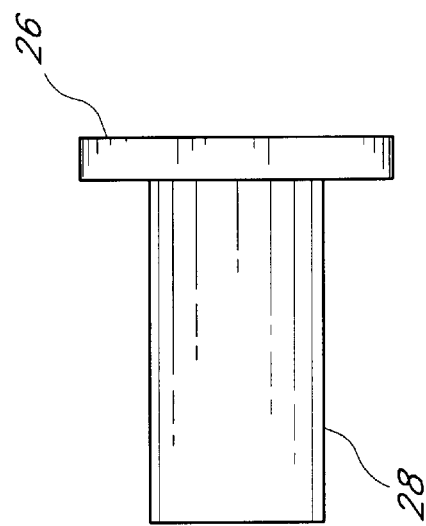
Figure 3A:
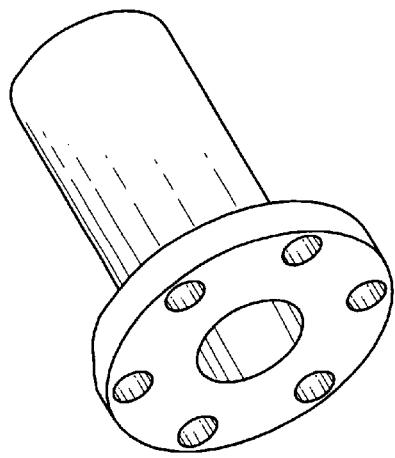
Figure 3B:
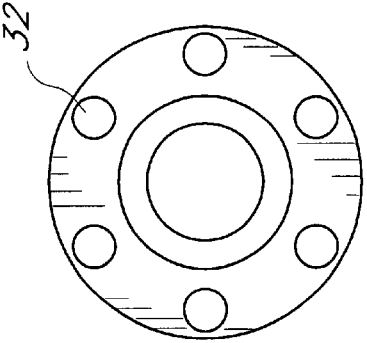

FIG. 1 shows the invention in its simplest preferred embodiment. The Figure includes several, but not all, of the improvements of present invention. Hydrogen peroxide and water vapor are present in a sterilization chamber 20. An ultraviolet light source 30 produces ultraviolet light at one end of an optical path 40. The ultraviolet light source can be a variety of lamps, including, but not restricted to, a deuterium lamp or a low pressure mercury lamp. The low pressure mercury lamp is preferred. The ultraviolet light source is stabilized by a current regulating lamp driver 50. The ultraviolet light passes along the optical path, is partially absorbed by the hydrogen peroxide, and is detected by the optical radiation detector 60. The optical path is defined by the ultraviolet light transmitted between the ultraviolet light source and the optical radiation detector. The signal from the optical radiation detector is converted in a current to voltage amplifier 70 and is processed and displayed in the conversion and display electronics 80. The ultraviolet light source 30 is housed in a thermally stabilized lamp housing 90. The optical radiation detector is housed in a thermally stabilized detector housing 100. The sterilization chamber 20 can be evacuated with a vacuum pump 110. Almost all of the components of this embodiment of the invention have improvements over the previous invention, as will become apparent as each of the components is described in more detail.

Sterilization Chamber

An example of a suitable sterilization chamber 20 is shown in FIG. 2. The sterilization chamber in the Figure is a cylinder with one rounded end and one flat end. The flat end has a door to provide an opening so that equipment can be placed inside the sterilization chamber for sterilization. Other types of sterilization chamber are suitable for use in the present invention. The application of this invention to these other types of sterilization chamber will be apparent to those skilled in the art. The sterilization chamber is made of material which is resistant to hydrogen peroxide vapor. Suitable materials include Aluminum T6061, 300 series stainless steel, or other suitable materials. Aluminum T6061 is a preferred material. The sterilization chamber includes a liquid or vapor sterilant inlet port 44 for introduction of hydrogen peroxide liquid or vapor and an exhaust port 46. The exhaust port 46 is connected to the vacuum pump 110. Optionally, a plasma electrode 34 (not shown) is present inside the sterilization chamber to allow for the generation of a plasma.

Optical Path

There are many ways to form the optical path 40 for transmission of optical radiation from the ultraviolet light source to the optical radiation detector. In one preferred embodiment, the optical path is formed by the dimensions and construction of the sterilization chamber 20. When it is desired to place one end of the optical path on a curved wall of the sterilization chamber, an aluminum flange 24 is welded onto the wall of the sterilization chamber. FIG. 3 shows an example of the aluminum flange 24. The aluminum flange is formed by welding a flange rim 26 onto a flange pipe 28. A series of flange holes 32 are drilled through the flange rim 26 as shown. The flange holes are threaded to allow for the attachment of optical equipment or plugging flanges.

Figure 4:
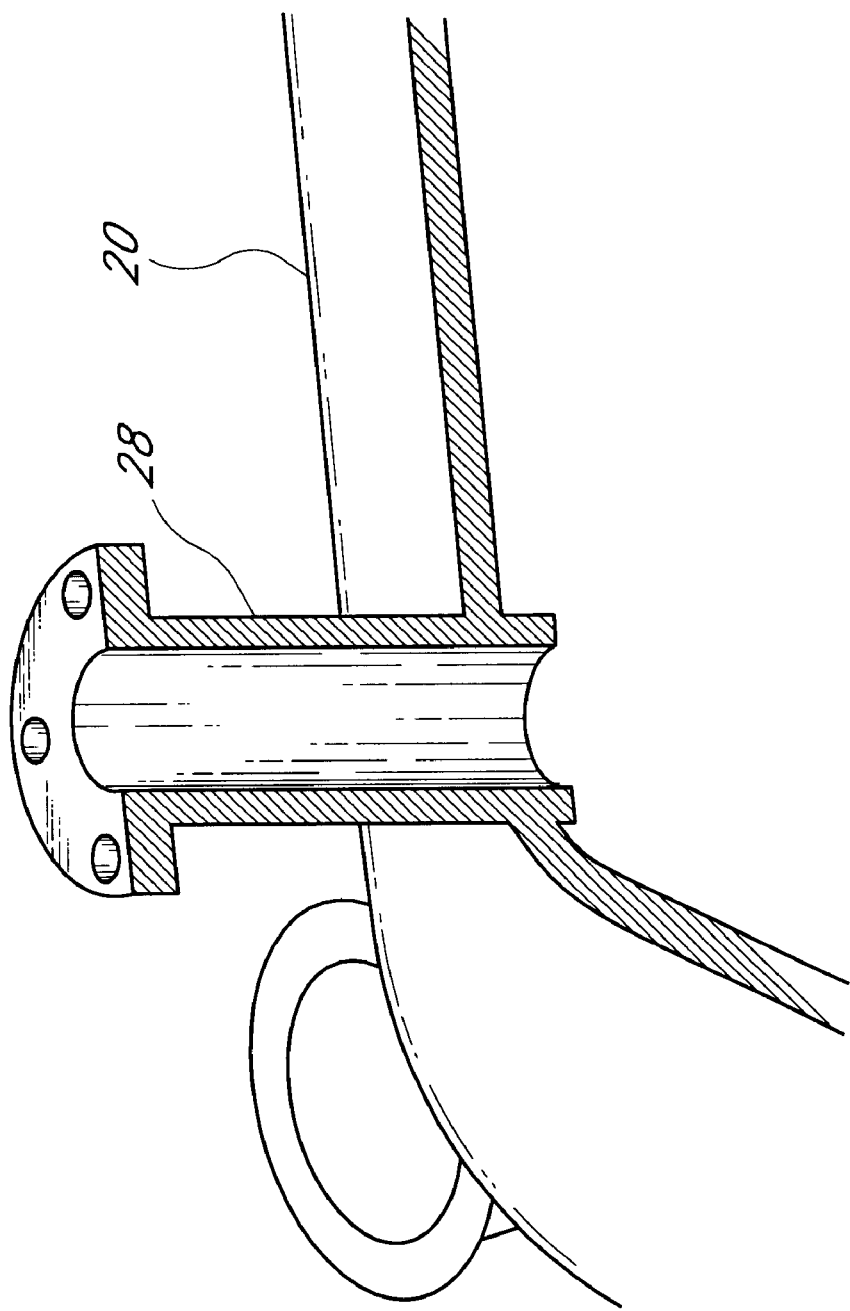
FIG. 4 is a perspective sectional drawing of a preferred method of attaching the aluminum flange to a curved wall of the sterilization chamber.

A preferred method of welding the aluminum flange 24 to the walls of the sterilization chamber 20 is shown in FIG. 4. A hole large enough to allow for the passage of the flange pipe 28 on the aluminum flange 24 is drilled through the wall of the sterilization chamber 20. The flange pipe 28 is pushed through the hole and is welded to the wall of the sterilization chamber so that the seal is vacuum tight.

Figure 5:
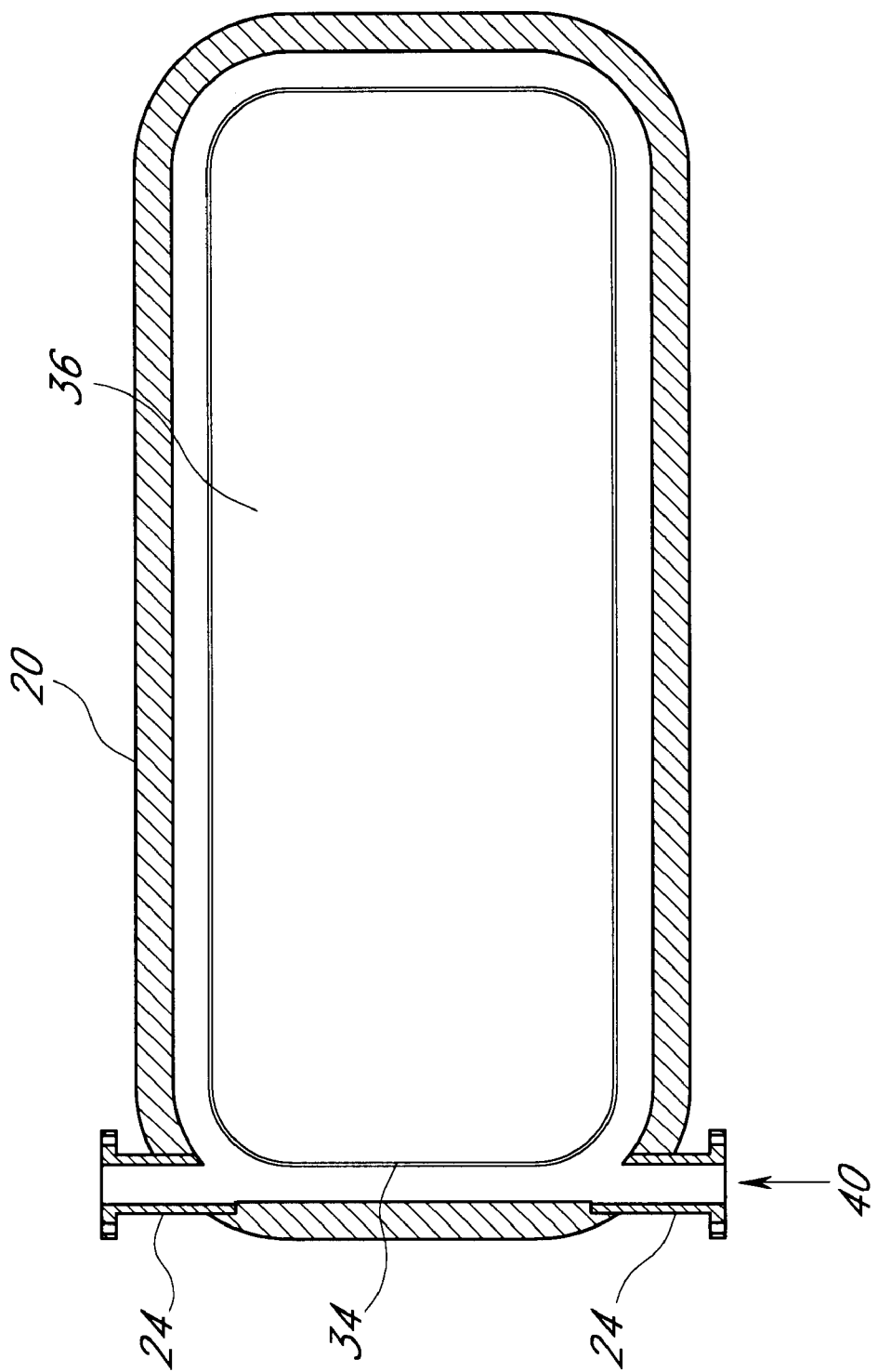
FIG. 5 is a sectional view of a preferred method of forming an optical path in the sterilization chamber on two curved walls along the short axis of the chamber.

One preferred method of forming the optical path 40 is shown in FIG. 5. Two aluminum flanges 24 are welded onto the sterilization chamber 20 so that the optical path 40 is along the short axis of the sterilization chamber. The plasma electrode 34 shown on the drawing is used when plasma is generated during the sterilization process. The plasma electrode is not continuous, and the optical path 40 is in fluid communication with the sterilization chamber interior 36. The optical path 40 is therefore exposed to a concentration of hydrogen peroxide which is representative of that in the sterilization chamber interior 36. Another view of this method of forming the optical path 40 with aluminum flanges 24 is shown on FIG. 2, where the two aluminum flanges comprising this configuration are labelled as 24A and 24B.

Figure 6:
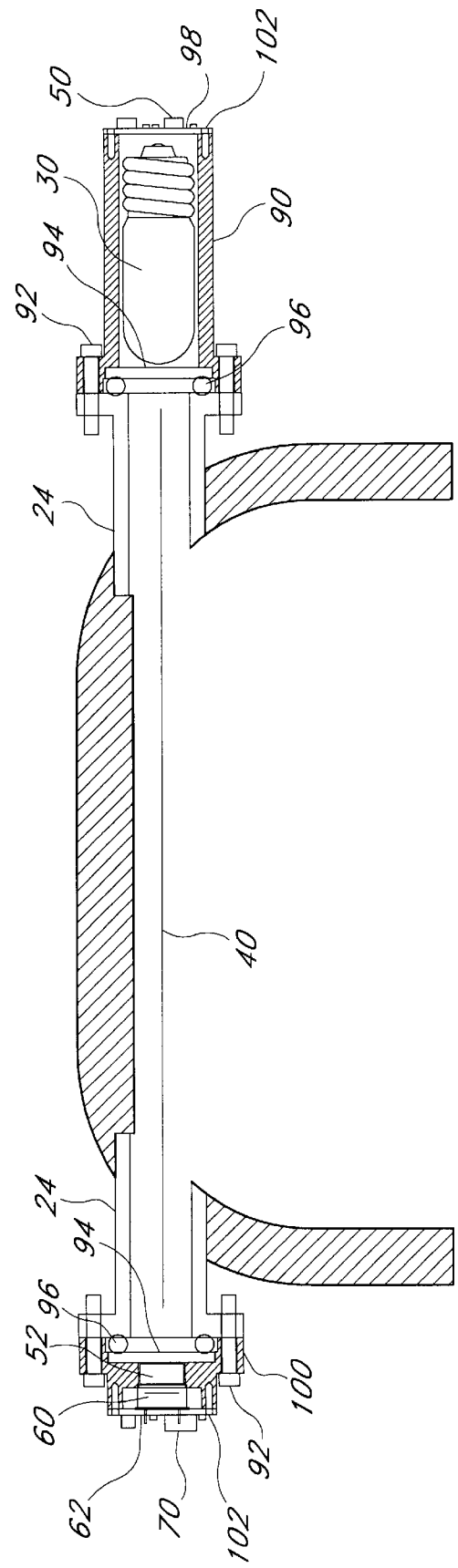
FIG. 6 is a sectional view of a preferred method of attaching the optical equipment to the optical path using aluminum flanges.

The thermally stabilized lamp housing 90 and the thermally stabilized detector housing 100 are attached to opposite ends of the optical path 40. One preferred method for the attachment of the optical equipment is shown in FIG. 6. The thermally stabilized lamp housing 90 is attached with a series of bolts 92 to the aluminum flange 24 on one end of the optical path 40, and the thermally stabilized detector housing 100 is similarly attached with bolts 92 to the aluminum flange 24 on the other end of the optical path 40. The ultraviolet light source 30 is placed in the thermally stabilized lamp housing 90 and is electrically connected to the lamp driver circuit board 98. The lamp driver circuit board is attached to the thermally stabilized lamp housing 90 with attachment screws 102. The current regulating lamp driver 50 is electrically connected to the lamp driver circuit board 98 to control the current delivered to the ultraviolet light source 30.

An optical window 94 is mounted on an O-ring 96 to isolate the sterilization chamber from the ultraviolet light source with a vacuum-tight seal. The optical window is constructed from a material with the ability to transmit ultraviolet radiation. The optical window must also be capable of withstanding the pressure of deep vacuum without breakage or distortion. In the preferred embodiment, the optical windows are made from ultraviolet grade fused silica. The O-rings 96 are made of a flexible material which does not degrade when exposed to hydrogen peroxide vapor. The preferred material for the O-rings is Viton TM, a polymer produced by DuPont. Use of the optical windows must include provisions for maintaining their temperature above the condensation threshold for the hydrogen peroxide/water mix at the expected operating concentration levels. In this design the optical windows are in thermal contact with the thermally stabilized lamp housing 90 to maintain their temperature.

The optical radiation detector 60 is housed in the thermally stabilized detector housing 100. The optical window 94 and the O-ring 96 isolate the optical radiation detector from the sterilization chamber with a vacuum-tight seal. An optional optical bandpass filter 52 may be placed between the optical radiation detector 60 and the optical window 94 as shown in FIG. 7 or alternatively between the ultraviolet light source 30 and the optical window 94 at the other end of the optical path. The optical bandpass filter allows the transmission of optical radiation at a particular band of wavelengths while rejecting all other wavelength components.

The detector circuit board 62 covers the optical radiation detector 60 and is attached to the thermally stabilized detector housing 100 with the attachment screws 102. The detector circuit board 62 is electrically connected with the optical radiation detector 60. The current to voltage amplifier 70 is attached to the detector circuit board 62 to convert the signal from the optical radiation detector 60 before processing in the conversion and display electronics 80.

FIG. 7 shows an alternative method of forming an optical path 40 and of attaching the thermally stabilized lamp housing 90 and the thermally stabilized detector housing 100 to the sterilization chamber 20. In this method, a mounting hole 42 is drilled through the wall of the sterilization chamber 20, and the thermally stabilized lamp housing 90 and the thermally stabilized detector housing 100 are attached directly to the wall of the sterilization chamber rather than being attached to the aluminum flange 24. The O-ring 96 is placed between the wall of the sterilization chamber and the optical window 94 to make a vacuum-tight seal. The bolts 92 fit into threaded holes in the wall of the sterilization chamber to securely attach the thermally stabilized lamp housing and the thermally stabilized detector housing to the wall of the sterilization chamber. When either the thermally stabilized lamp housing or the thermally stabilized detector housing is to be attached to a flat wall of the sterilization chamber, the attachment method shown in FIG. 7 is preferred. The attachment method of FIG. 6 using an aluminum flange 24 may also be used, but is not preferred, when the optical housings are attached to a flat wall of the sterilization chamber. If both the thermally stabilized lamp housing 90 and the thermally stabilized detector 100 housing are to be attached to flat walls of the sterilization chamber with the method shown in FIG. 7 to form an optical path 40, the two mounting holes 42 must be on opposite walls of the sterilization chamber, the two walls where the mounting holes are drilled must be parallel, and the two mounting holes must be located in alignment so that an optical path 40 exists between the two holes. The optical path is defined by the ultraviolet light path between the ultraviolet light source 30 and the optical radiation detector 60.

Some of the preferred embodiments of the present invention require the use of more than one optical path. Any of the described methods of the present invention may be used to form the additional optical paths.

Another preferred attachment method for the optical housings uses the attachment method of FIG. 6 with the aluminum flange 24 on one end of the optical path 40 and the attachment method of FIG. 7 with the mounting hole 42 on the other end. The thermally stabilized lamp housing 90 is attached to either the aluminum flange 24 or the mounting hole 42, and the thermally stabilized detector housing 100 is attached to whichever device is not used for attachment of the thermally stabilized lamp housing. Any of the described attachment methods for the optical equipment which forms an optical path 40 between the ultraviolet light source 30 and the optical radiation detector 60 may be used as a part of the preferred embodiment of this invention. Other suitable attachment methods may also be employed as part of the present invention.

None of the described attachment methods for the optical equipment such as the ultraviolet light source and the optical radiation detector include focussing devices such as lenses, although the use of focussing devices such as lenses is part of the embodiment of the present invention. The use of focussing devices is not part of the preferred embodiment, because optical alignment is not as critical if one does not use such focussing devices. By not using focussing devices, the diameter of the light beam from the ultraviolet light source is far larger than the size of the receiving optical radiation detector at the other end of the optical path. The present invention is therefore forgiving if either the ultraviolet light source or the optical radiation detector is manufactured or assembled out of alignment. A system containing focussing devices such as lenses would not be so forgiving of perturbations to the optical equipment. The ultraviolet light source 30 is preferably connected electrically to a current regulating lamp driver 50. Operation with a regulating, constant-current driver allows for stable ultraviolet output of the lamp. In the present invention, it is required that the optical output of the light source remains constant during operation for accurate results.

Current Regulating Lamp Driver

The ultraviolet light source 30 is preferably connected electrically to a current regulating lamp driver 50. Operation with a regulating, constant-current driver allows for stable ultraviolet output of the lamp. In the present invention, it is required that the optical output of the light source remains constant during operation for accurate results.

Figure 8:
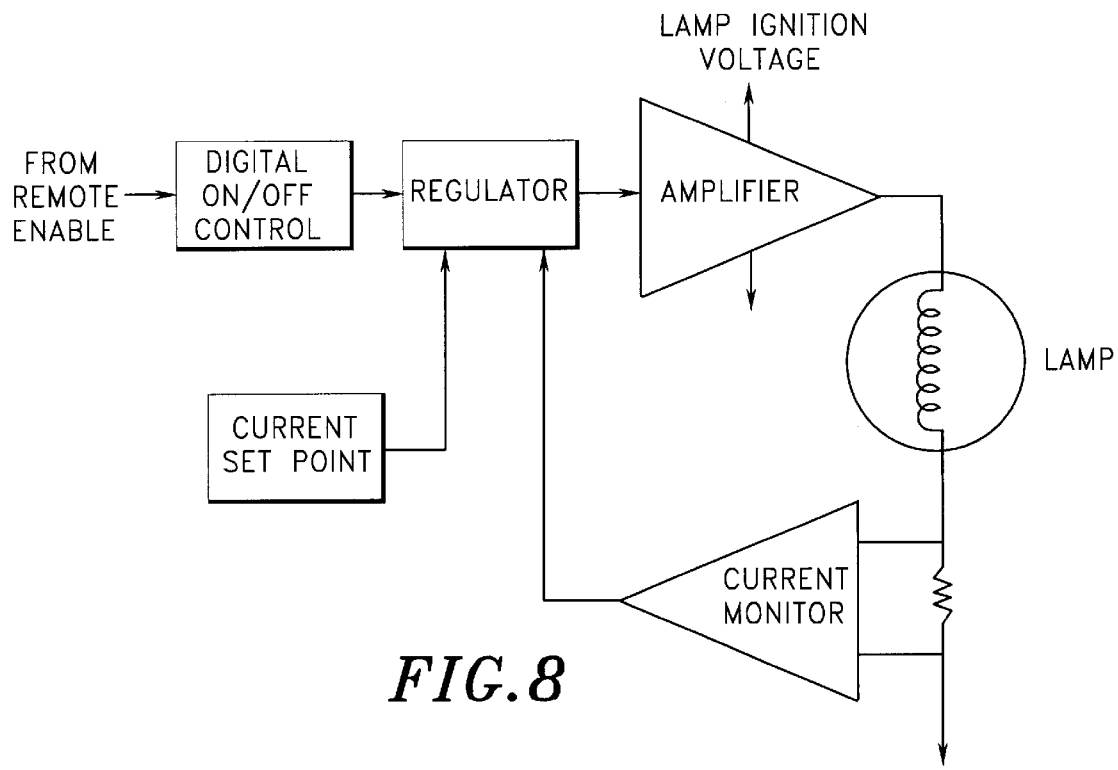
FIG. 8 is a schematic diagram of a current regulating lamp driver circuit.

This device is another improvement of the present invention. Many lamps are driven with a voltage regulating lamp driver. When the ultraviolet light source is driven with the current regulating lamp driver, the output light of the ultraviolet light source is more stable than when it is driven with a voltage regulating lamp driver. Use of the current regulating lamp driver is therefore part of the preferred embodiment of the present invention. The circuit diagram for the current regulating lamp driver is shown in FIG. 8. In addition to regulating the amount of current to the ultraviolet lamp, the lamp driver allows for the increased terminal voltage required for igniting the lamp the lamp before transitioning into a steady or constant current mode. The circuit also allows for digital control of the lamp's optical state, either on or off.

Optical Radiation Detector

After the ultraviolet radiation from the ultraviolet light source passes through the sample, it is detected with the optical radiation detector 60. Under the preferred embodiment of the present invention, the optical radiation detector is an optical detector suitable for detecting ultraviolet light. Although there are many suitable detectors available, the detector used in the present system is a silicon photodiode type detector with an active area of 5.8×5.8 mm. The detector is housed in a TO-8 package with a quartz window. Other detectors are suitable, including CCD arrays, photodiode arrays and photomultiplier tubes.

Detection/Signal Processing Electronics

Figure 9:
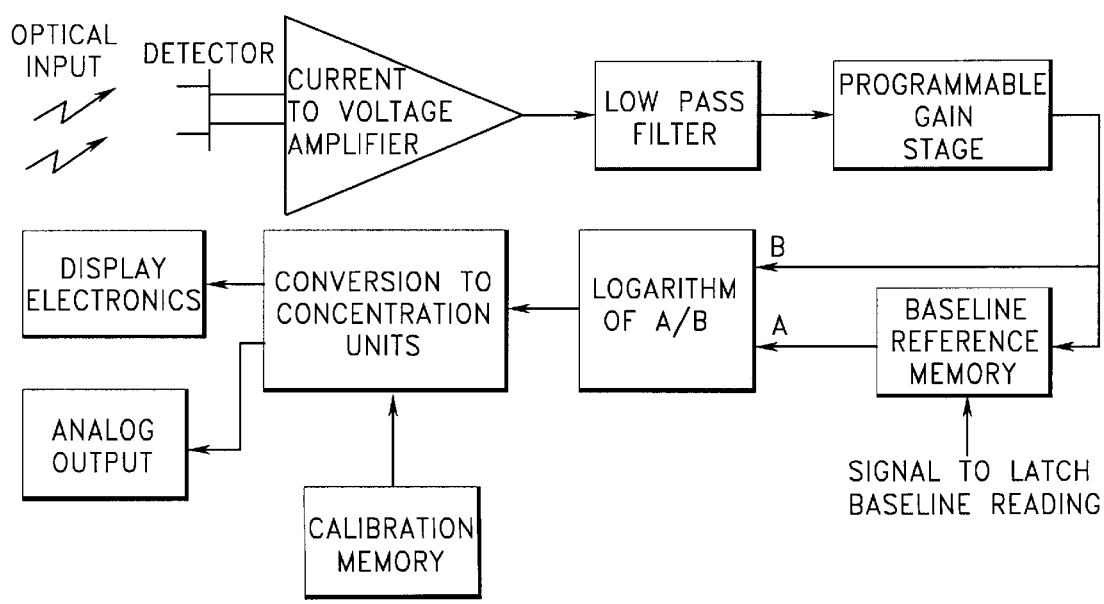
FIG. 9 is a schematic diagram of the detector and signal processing electronics.

After the ultraviolet radiation is detected by the optical radiation detector, the detector signal must be processed. The detection and signal processing electronics are shown in FIG. 9.

Movable Gas Cell

In all of the above embodiments, both the ultraviolet light source 30 and the optical radiation detector 60 are fixed to one location on the walls of the sterilization chamber 20. The thermally stabilized lamp housing 90 and the thermally stabilized detector housing 100 are attached to the aluminum flange 24, as shown in FIG. 6, or are attached directly to the sterilization chamber wall on the mounting hole 42, as shown in FIG. 7. Relocation of either the thermally stabilized lamp housing 90 or the thermally stabilized detector housing 100 to another position on the sterilization chamber would require the addition of aluminum flanges 24 or mounting holes 42 to the sterilization chamber at locations which form an optical path going through the area to be monitored. The addition of an aluminum flange or a mounting hole requires extensive machining and/or welding. Even if the aluminum flanges or mounting holes are added to the sterilization chamber, equipment which is placed in the sterilization chamber to be sterilized may block the optical path 40, preventing the measurement of the hydrogen peroxide vapor concentration. A more flexible method of mounting the optical equipment is therefore desirable in order to allow measurements of hydrogen peroxide vapor concentrations to be taken at various locations inside the sterilization chamber without the need to make extensive modifications to the sterilization chamber.

Figure 10:
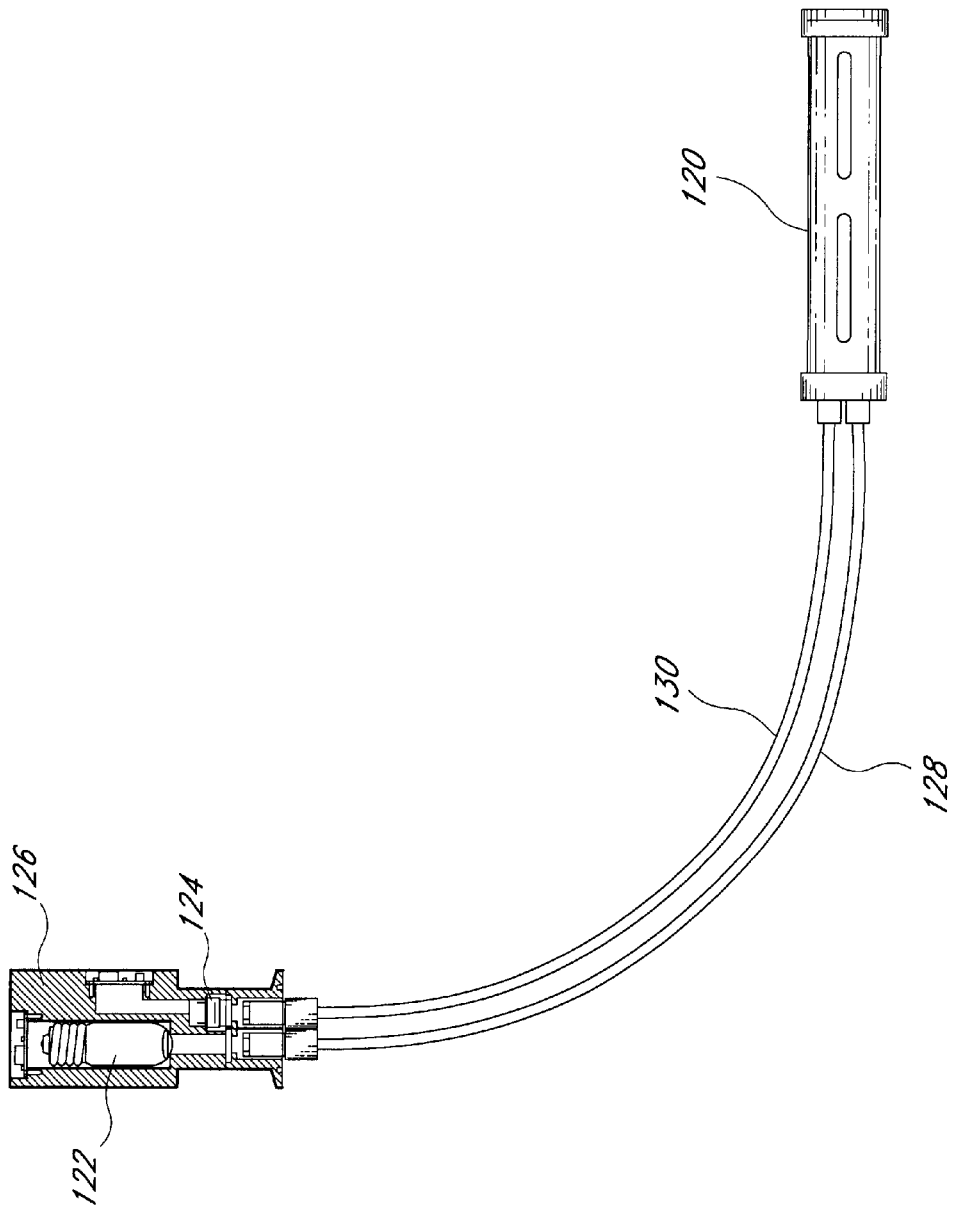
FIG. 10 is a side view of a movable gas cell suitable for use with the system of FIG. 1.

FIG. 10 shows a diagram of a movable gas cell 120 and associated equipment for determination of hydrogen peroxide vapor at various locations throughout the sterilization chamber. An ultraviolet bulb 122 and a detector 124 are contained in a lamp/detector housing 126. One end of a first optical fiber 128 is attached to the ultraviolet bulb 122. The other end of the first optical fiber 128 is connected to a first end of the movable gas cell 120 so that light is conducted from the ultraviolet bulb 122 through the first optical fiber 128 into the movable gas cell and travels the length of the cell. One end of a second optical fiber 130 is attached to the detector 124. The other end of the second optical fiber 130 is connected to the second end of the movable gas cell such that the light from the first optical fiber 128 is transmitted the length of the movable gas cell 120 and is received by the second optical fiber 130. The second optical fiber 130 transmits the received light to the detector 124, where the received light is converted to an electrical signal. The electrical signal from the detector 124 is sent to the current to voltage amplifier 70 and then to the conversion and display electronics 80. The ends of the two optical fibers 128 and 130 are oriented and aligned so that the movable gas cell 120 provides an optical path 40 with a fixed optical length between the ends of the optical fibers 128 and 130. The is movable gas cell 120 contains openings so that the interior of the movable gas cell is in fluid communication with the atmosphere of the sterilization chamber so that the gas in the movable gas cell is representative of the gas in the immediate area in the sterilization chamber.

Figures 11A, 11B, 11C:
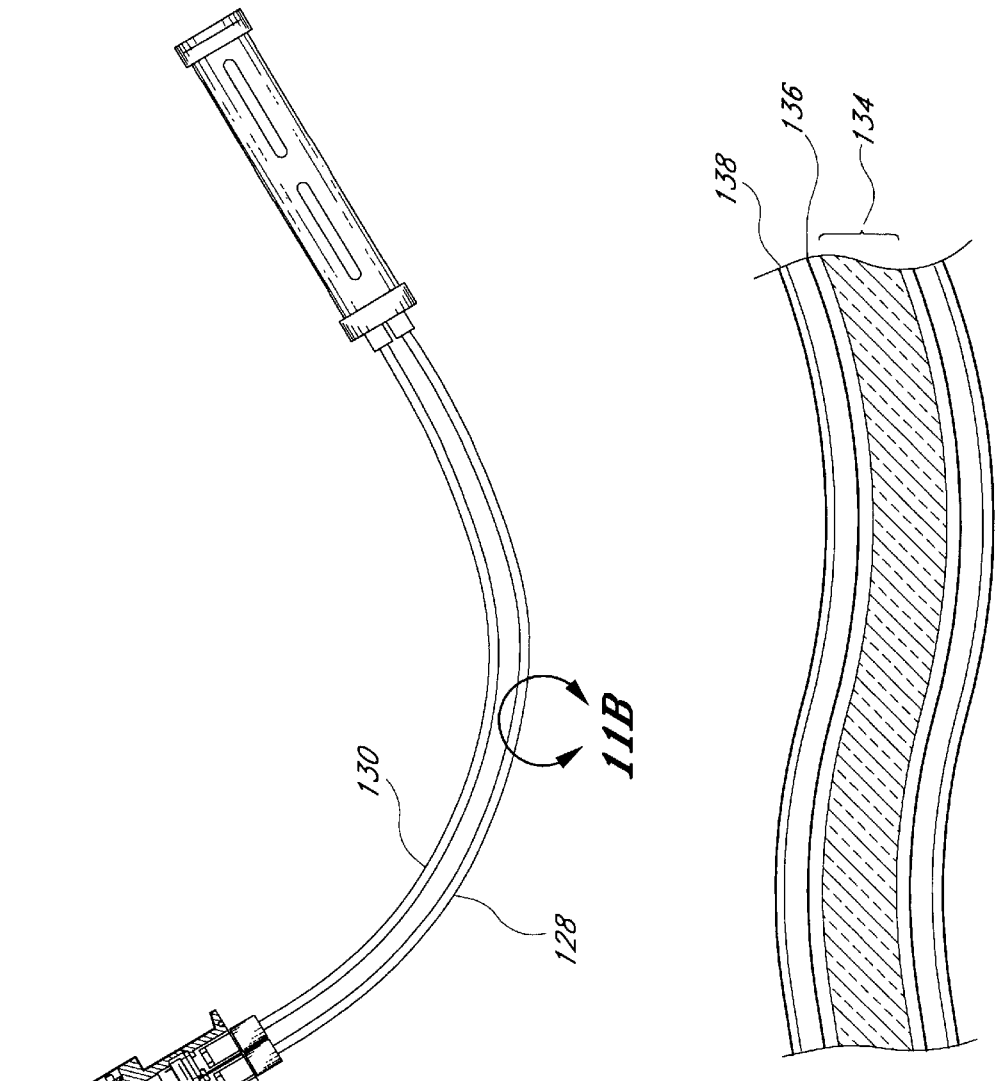
FIG. 11A is a view of the movable gas cell showing the portion which is shown in greater detail in FIG. 11B and FIG. 11C.
FIG. 11B is a sectional view of an optical fiber of the movable gas cell along the long axis.
FIG. 11C is a cross sectional view of an optical fiber.

The movable gas cell is constructed of materials that do not interact with hydrogen peroxide gas. These materials include Aluminum T6061, 300 series stainless steel, Teflon, or glass. To allow for flexibility, the active area of the optical fibers 128 and 130 is composed through the bundling of smaller fibers 132, typically between $100 \times 10^{-6}$ meters and $1500 \times 10^{-6}$ meters but most preferably $100 \times 10^{-6}$ meters in diameter. These smaller fibers 132 are arranged to form a fiber bundle 134, shown in FIG. 11C, with larger active area between 0.010 inches and 0.5 inches in diameter, but most preferably 0.125 inches in diameter. The smaller fiber's core is made of quartz capable of optical transmission in the ultraviolet. Each individual smaller fiber is clad with fluorine doped silica for its optical characteristics and coated with a polyimide to increase the fiber's strength. However, this polyimide coating is reactive with hydrogen peroxide. It is because of this reaction that it is necessary to keep the fiber coating from coming into contact with the hydrogen peroxide within the chamber that is being monitored. For this purpose, a Teflon sleeve 136 is secured around the fiber bundle 134 within the space existing between the fiber bundle 134 and the outer stainless steel interlocking protective jacket 138. FIGS. 11B and 11C show how the smaller fibers 132 are bundled together to form a fiber bundle 134 and are covered with the Teflon sleeve 136 and stainless steel interlock 138. In FIG. 11B, the fiber bundle 134 is shown with a glass code because of the combined quartz and fluorine doped cores. The optical fibers 128 and 130 are preferably 0.5–20 meters in length, but may be up to at least 200 meters in length. It is most preferred that the optical fibers are 1 meter in length.

In other embodiments, the movable gas cell can contain reflective or refractive optics to direct the optical radiation in such a path as to increase the effective exposed pathlength of the optical radiation while not increasing the physical size of the cell. Other embodiments of the movable cell include all of the embodiments of the various forms of spectrophotometers, to be discussed in detail later, including the single beam ultraviolet spectrophotometer, the single beam ultraviolet spectrophotometer with interference filter, the dual beam ultraviolet spectrophotometer, and the variations on these embodiments.

Figure 12:
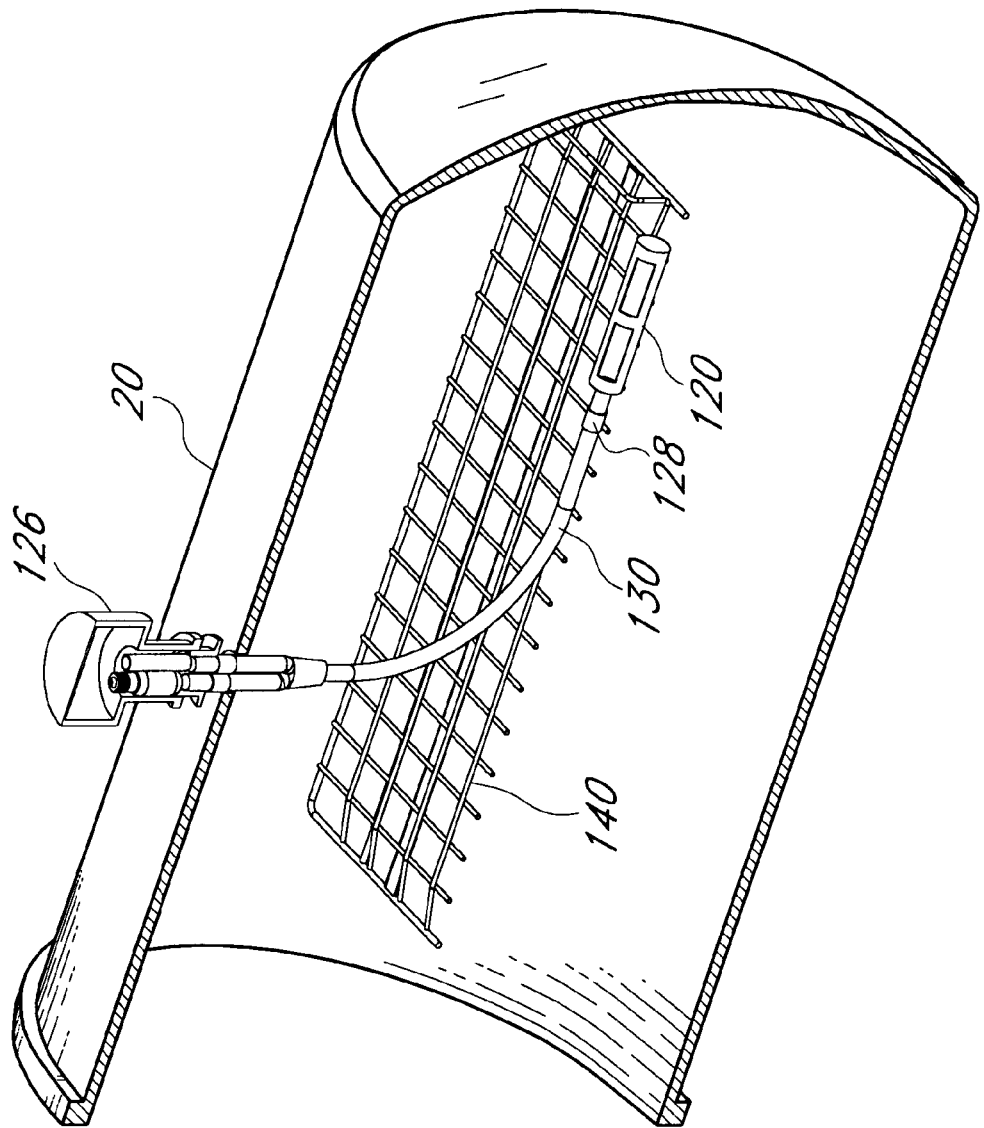
FIG. 12 is a perspective view demonstrating the use of the movable gas cell. of FIG. 10.

Use of the movable gas cell is demonstrated in FIG. 12. The gas cell 120 is shown inside the sterilization chamber 20 on an equipment rack 140. The lamp/detector housing 126 is mounted on the sterilization chamber through the use-of a KF style vacuum fitting at any location that will not interfere with normal operation of the sterilizer. FIG. 12 shows an alternative configuration for the movable gas cell in which the two optical fibers 128 and 130 are housed in a sheath and are thus not visible in the Figure. The ultraviolet bulb 122 is preferably connected to the current regulating lamp driver 50, and the detector 124 is connected to the current to voltage amplifier 70 and the conversion and display electronics 80. By using this configuration, the concentration of hydrogen peroxide vapor on top of the equipment rack 140 can be determined with the movable gas cell 120 with the method of the present invention. It would be almost impossible to locate optical equipment externally in a manner shown in FIGS. 6–7 or in the manner of the other external attachment embodiments to obtain a measurement of the concentration of hydrogen peroxide vapor in the area of the equipment rack. It is almost certain that either the equipment rack 140 or equipment placed on the rack for sterilization would block the optical path 40 between the ultraviolet light source 30 and the optical radiation detector 60.

The present method of measuring the concentration of vapor phase hydrogen peroxide vapor is a spectrophotometric determination using the ultraviolet light source 30 and the optical radiation detector 60 to measure the absorbance A in the ultraviolet region. Although the ultraviolet region extends from 4–400 nm (nanometers), air absorbs ultraviolet light below about 200 nm. The ultraviolet region below 200 nm is therefore called the extreme ultraviolet, and the air must be removed from the apparatus to operate in this region. The region from 200–300 nm is the far ultraviolet, and the region from 300–400 nm is the near ultraviolet. It is preferred in the present invention to use an ultraviolet light source which operates in the near or far ultraviolet regions, from 200–400 nm.

The concentration of hydrogen peroxide vapor is calculated using Beer's law, which states that $A=\epsilon lc$, where $\epsilon$ is the extinction coefficient of a substance at the measured wavelength, l is the sample length, and c is the concentration of the substance being measured in the sample. In the present invention, the sample length is the length of the optical path 40. Beer's law assumes that the light is monochromatic, that it be of a single wavelength.

Alternatively, the concentration may be determined from a calibration curve of absorbance versus the concentration of hydrogen peroxide vapor. The procedure for obtaining this calibration curve is described under Example 1 below.

There are at least two complicating factors in determining the concentration of hydrogen peroxide vapor spectrophotometrically. First, any substance which absorbs at the chosen wavelength will contribute to the absorbance and thus potentially interferes with the determination of the concentration of hydrogen peroxide vapor. Second, the ultraviolet light source 30 does not emit light at a single wavelength. The emission spectrum of the ultraviolet light source is dependent on the ultraviolet light source type. The emission spectra may be broad or contain multiple peaks. As a result there may be deviations from Beer's law. The present invention employs several different methods which can minimize both problems. The issue of interferences will be discussed first.

The previous invention analyzes hydrogen peroxide spectrophotometrically with a light source in the near infrared (NLR) region. Hydrogen peroxide has a strong S absorption peak centered at approximately 1420 mn in the NIR Water also has an absorption in the same region. There is thus an interference between the hydrogen peroxide and water peaks, because the absorbance at 1420 nm is due to a combination of water vapor and hydrogen peroxide vapor. In the previous invention, the concentration of water in the sample is determined spectrophotometrically in another region of the NIR where hydrogen peroxide does not have an absorption peak, and the contribution to the absorbance at 1420 nm from the determined concentration of water is subtracted from the total absorbance at 1420 nm to determine the absorbance due to hydrogen peroxide. The concentration of hydrogen peroxide vapor can then be calculated using the corrected absorbance and Beer's law.

Figure 13:
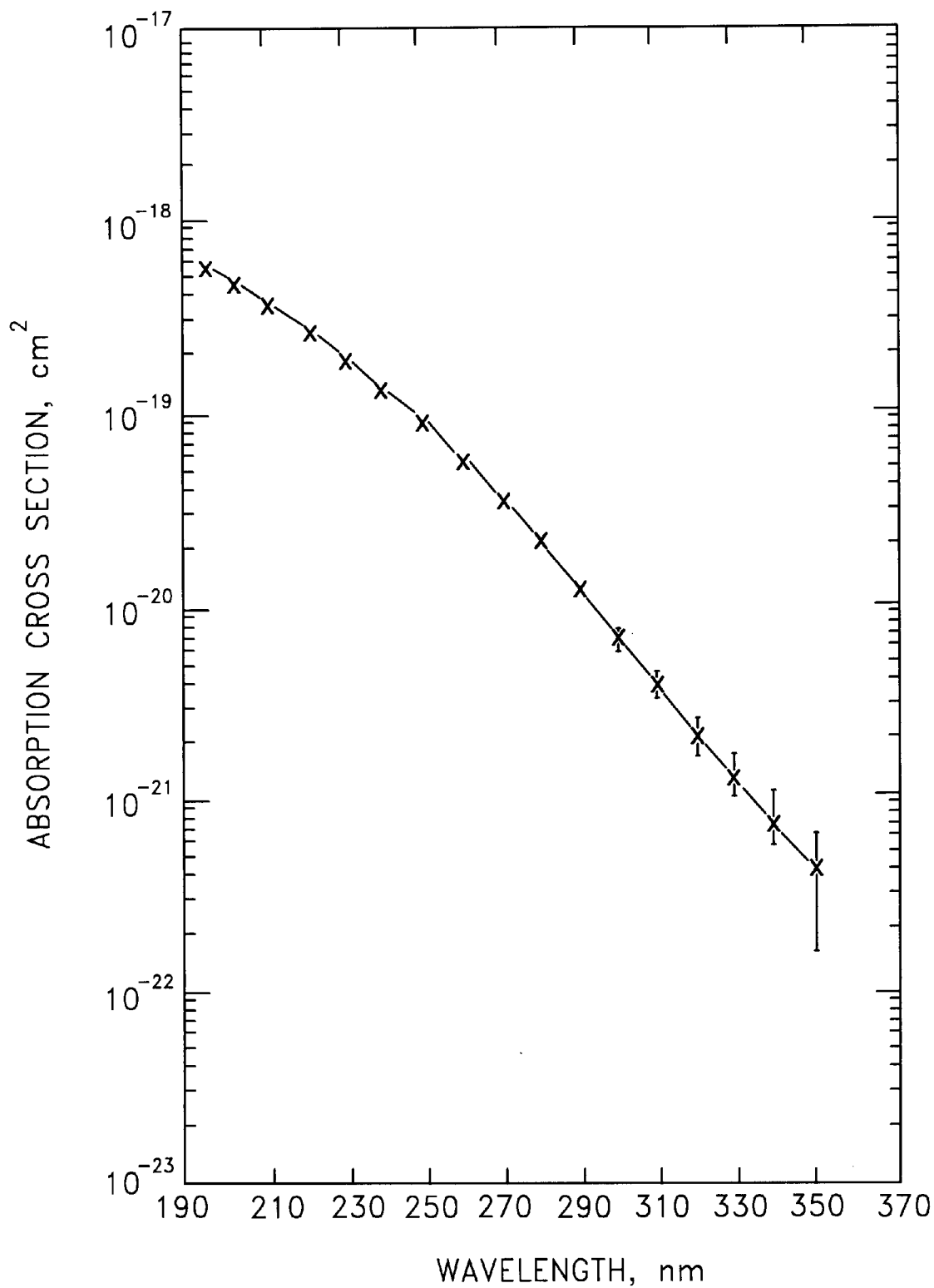
FIG. 13 is a graph of the absorption spectrum of hydrogen peroxide vapor in he ultraviolet region.

In the present invention, an ultraviolet light source is used rather than an NIR light source. The absorption spectrum of hydrogen peroxide vapor in the ultraviolet region is shown in FIG. 13. The absorption band extends strongly from 190–300 nm. Water vapor does not absorb in this region. There is therefore no need to subtract the absorbance due to water from the hydrogen peroxide absorbance, as in the previous invention, because there is no interference between the two compounds in the ultraviolet region. The use of an ultraviolet light source rather than a NIR light source is a major improvement of the present invention over the previous invention. The data analysis is simpler, and the electronics can be simpler and less expensive.

There is a remaining interference with the hydrogen peroxide absorbance in the ultraviolet region. Many organic molecules have broad, intense absorption peaks in the ultraviolet region. Organic molecules may be present in the sterilization chamber due to outgassing or the presence of organic solvents. It is difficult to determine the concentration of the organic molecules and subtract their contribution to the absorption in the ultraviolet using a method similar to the previous invention for two reasons. First, the absorption peaks of both the hydrogen peroxide and the organic molecules in the ultraviolet are very broad. It is very difficult or impossible to find a region of the ultraviolet where the peaks do not overlap. One cannot easily determine the concentration of the organic molecules using nonoverlapping peaks, as in the previous invention. Second, each organic molecule has a different absorption peak with a different extinction coefficient. If one does not know what organic molecule is present, one does not know what correction should be made on the ultraviolet absorbance. It is therefore difficult to correct the hydrogen peroxide absorbance in the ultraviolet region for the contribution due to organic molecules.

In the present invention, the interference from the organic molecules is removed by evacuating the sterilization chamber through the exhaust port 46 using the vacuum pump 110 until a vacuum of 500 millitorr is reached. This vacuum may range from 0 to 50 torr, more preferably from 0 to 10 torr, and most preferably from 0 to 1 torr. At this point, radio frequency plasma may be run to disassociate any remaining hydrogen peroxide vapor into water and oxygen. This may require that the plasma operate between 1 and 15 minutes. At this point the vacuum pump may again continue to evacuate the chamber to the desired initial pressure, most preferably from 0 to 1 torr. The absorbance of the present condition of the chamber is then measured. This is the baseline reference. It establishes a baseline for the system such that a signal above the baseline reference is due to an absorbing species in the optical path.

In order to confirm that any potential sources of interfering gas that may exist within the chamber prior to the injection of hydrogen peroxide do not interfere with the measurement of hydrogen peroxide, the baseline absorbance reading is monitored for 5 to 60 seconds. During this time, the throttle valve is closed and both the pressure and absorbance are recorded. If the absorbance changes by an amount greater than a predetermined maximum the system is declared unstable and further high vacuum treatment or radio frequency plasma may be necessary. This may occur if the load to be sterilized is releasing a gas that also absorbs at the measuring wavelength, for example.

The previous system evacuates the sterilization chamber only to a pressure of 20 torr or less when obtaining a baseline reference. Evacuating the system to a lower pressure of 500 millitorr in the present invention removes more of the organic molecules, reducing the amount of interference with the hydrogen peroxide absorption band. Evacuating to 20 torr removes 97% of the atmosphere. Evacuating to 500 millitorr removes 99.93% (759.5 torr/760 torr) of the atmosphere, significantly more than the previous invention. Some organic molecules have strong absorption peaks in the ultraviolet region, and even a small amount of organic compound remaining could interfere with the determination of hydrogen peroxide vapor.

The success of the present invention for determining the concentration of hydrogen peroxide by using an ultraviolet light source depends on a series of improvements which make the determination practical: 1. Removing the interfering organic species to a high degree by using a high vacuum treatment of 500 millitorr and 2. Establishing of a zero baseline for hydrogen peroxide through the use of radio frequency plasma to disassociate any hydrogen peroxide vapor present at or below 500 millitorr. Both are part of the preferred embodiment of this invention and part of a series of improvements of the present invention.

Figure 14A:
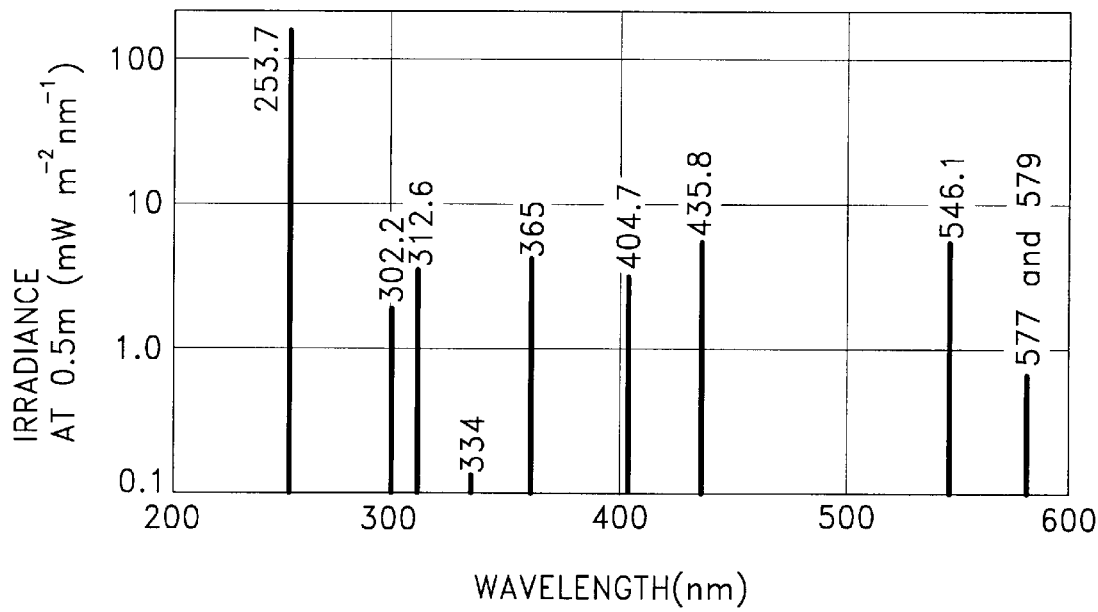
FIG. 14A is a graph of the output spectrum for a low pressure mercury lamp.
Figure 14B:
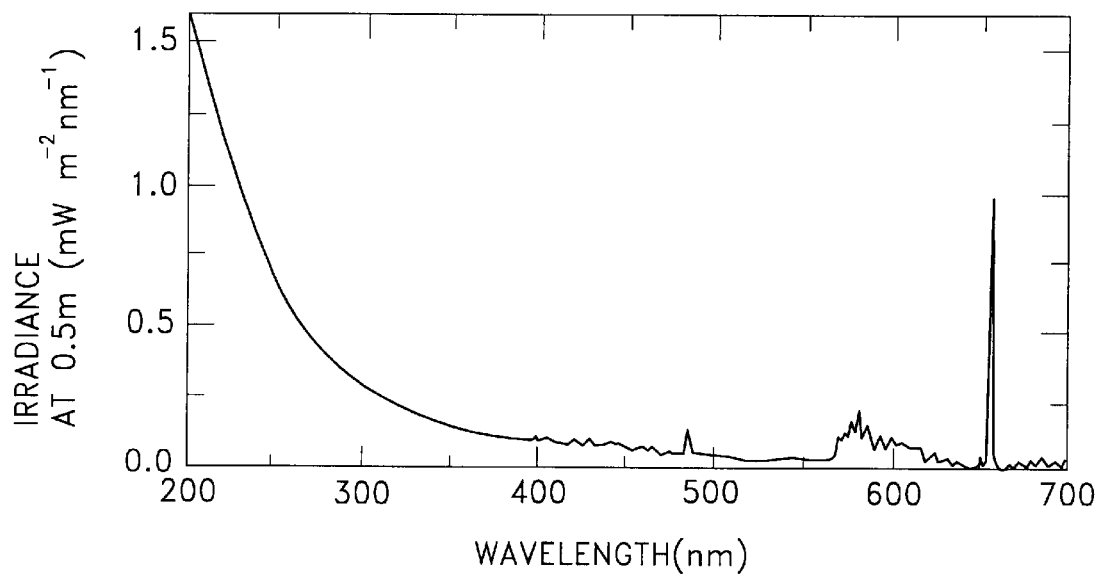
FIG. 14B is a graph of the output spectrum for a deuterium lamp.

The emission characteristics of the ultraviolet light source are another potential complication with the spectrophotometric determination of hydrogen peroxide in the ultraviolet region. The ultraviolet light source does not emit light at a single wavelength, but at multiple wavelengths. For example, a typical output spectrum for a low pressure mercury vapor lamp is given in FIG. 14A. The principal emission line is at 253.7 nm (usually rounded to 254 nm), a region in which hydrogen peroxide absorbs strongly, and water does not absorb. As shown on FIG. 14A, many other emission peaks are present, although they are far less intense than the principal peak at 234 nm. (Note that the vertical scale on FIG. 14A is a logarithmic scale, and the smaller emission peaks are not as large as they first appear.) The emission spectrum for a deuterium lamp is shown in FIG. 14B. The lamp emits light in a broad band in the ultraviolet, extending from less than 200 nm to about 350 nm, with a tail extending beyond. The multiple emission peaks of the low pressure mercury vapor lamp and the broad emission band of the deuterium lamp can lead to deviations from Beer's law. The present invention provides means to minimize the effects from the fact that the ultraviolet light source is not monochromatic.

In the simplest embodiment of this invention, the fall spectrum of the ultraviolet light source 30 is collected by the optical radiation detector 60. The radiation spectrum is only limited by the spectral characteristics of the optical windows and the optical radiation detector. This embodiment may be referred to as the single beam ultraviolet spectrophotometer. Radiation collected by the optical radiation detector is integrated with respect to its wavelength dependent quantum efficiency. The output of the optical radiation detector is thus a summation of the photon count for each spectral wavelength reaching the detector multiplied by the radiation detector's quantum efficiency at that specific wavelength. Dependent upon the spectral characteristics of the ultraviolet light source, the output of the optical radiation detector may be due to a group of wavelengths that are absorbed by the hydrogen peroxide vapor in the optical path and other wavelengths that are not absorbed by the hydrogen peroxide vapor in the optical path. In terms of the system output response, the nonabsorbing wavelengths act as stray light in the system and limit the measurement of the true absorbance resulting in deviations from Beer's law. This may not be a problem if there is a proper calibration of the conversion between absorbance and concentration of hydrogen peroxide for the particular optical source being used. The long term accuracy of this approach depends on the stability of the spectral intensities of the ultraviolet light source and the response of the optical radiation detector. Specifically, the total amount of non-absorbing light converted by the optical radiation detector needs to remain constant over time. The response of the optical radiation detector is affected by temperature changes. Temperature changes must therefore be minimized. The present invention provides means to minimize changes in both the output spectrum of the ultraviolet radiation source and the response of the optical radiation detector with respect to both time and temperature.

The stability of the output of the ultraviolet radiation source is insured in two ways. First, in the preferred embodiment of this invention, the power supply is driven with the current regulating lamp driver 50 rather than the conventional voltage regulating lamp driver. When controlled by the current regulating lamp driver, the output spectrum of the ultraviolet light source is more stable than when it is controlled with a voltage regulating lamp driver. The stability of the ultraviolet light source is important in all of the embodiments of the present invention but is especially important in the embodiment of the single beam ultraviolet spectrophotometer, where the full spectrum of the ultraviolet light source is collected by the optical radiation detector, because any change in the output source will affect the validity of the calibration between absorbance and the concentration of hydrogen peroxide. The use of the current regulating lamp driver to stabilize the ultraviolet radiation source is one of the important improvements of the present invention and is part of the preferred embodiment.

The second way the stability of the ultraviolet light source is optimized is by minimizing the changes in temperature experienced by the light source. The output spectrum of both the deuterium lamp and the low pressure mercury vapor lamp change with temperature. The temperature changes experienced by the ultraviolet light source should therefore be minimized.

The mode of attachment of the ultraviolet light source 30 to the sterilization chamber inherently minimizes temperature changes. Thus, the ultraviolet light source is housed in the thermally stabilized lamp housing 90. In turn, the thermally stabilized lamp housing is attached directly to the wall of the sterilization chamber 20 through the mounting hole 42 or indirectly through the aluminum flange 24. The sterilization chamber is large and very heavy. The sterilization chamber, the thermally stabilized lamp housing, and the aluminum flange are all normally fabricated from aluminum, a highly thermally conducting metal. The thermally stabilized lamp housing 90 is in direct thermal contact with a large mass of highly conducting aluminum metal, the sterilization chamber 20. The sterilization chamber therefore acts as a large heat sink to stabilize the temperatures of both the thermally stabilized lamp housing and the ultraviolet light source. The high thermal stability of the ultraviolet light source as a result of its attachment mode to the sterilization chamber is an important improvement of the present invention and part of the preferred embodiment.

The response of the optical radiation detector is also temperature dependent. Maintaining the optical radiation detector at constant temperature is therefore important in maintaining stability of the response of the detector. Just as for the thermally stabilized light housing, the thermally stabilized detector housing is in direct thermal contact with the massive sterilization chamber. Housing the optical radiation detector in the thermally stabilized detector housing therefore maintains constant temperature due to its being in contact with the large heat sink sterilization chamber. The temperature stability of the optical radiation detector due to its method of attachment to the sterilization chamber is another improvement of the present invention and is part of the preferred embodiment.

The most preferred embodiment when operating as a single beam ultraviolet spectrophotometer comprises use of the low pressure mercury lamp as an ultraviolet light source with the current regulating lamp driver and use of the thermally stabilized lamp housing and thermally stabilized detector housing to maintain temperature stability of both the ultraviolet light source and the optical radiation detector. Although the invention is operative without the use of all of these improvements in combination, the combination of improvements is the most preferred embodiment. The low pressure mercury lamp as the ultraviolet light source provides a light source with a strong principal emission peak at 254 nm. Because the emission peak at 254 nm is so strong, the deviations from Beer's law due to the presence of other emission peaks is less than for other ultraviolet light sources with more diffuse emission spectra. There is thus less need for filters to remove other wavelengths when using the low pressure mercury vapor lamp than for other ultraviolet light sources. The temperature stabilized lamp housing and detector housing minimize the temperature changes in the ultraviolet light source and optical radiation detector, minimizing the changes in the output spectrum and optical response due to temperature effects. Use of the current regulating lamp driver provides additional stability to the output of the low pressure mercury vapor lamp. The stability of the output of the ultraviolet light source and the response of the optical radiation detector are especially important when operating in the embodiment of single beam ultraviolet spectrophotometer, because there are no filters or other means of compensating for changes in either. The other methods of operation have means of at least partially compensating for these changes.

In another embodiment of the present invention, an optical bandpass filter is placed next to the ultraviolet light source or next to the optical radiation detector. This embodiment may be referred to as the single beam ultraviolet spectrophotometer with interference filter. The particular location of the optical bandpass filter may depend on the amount of heat produced by the ultraviolet light source and the amount of stray light in the system. FIG. 6 shows one form of this embodiment with the optical bandpass filter 52 located next to the optical radiation detector 60. The design of the optical bandpass filter allows for the transmission of optical radiation at a small particular band of wavelengths while rejecting all other wavelength components. The optical bandpass filter allows the detector to measure optical radiation from only a select band of wavelengths emitted by the source and allowed to pass through the optical filter. The optical bandpass filter limits any effects due to stray light, namely deviations from true and measured absorbance values, and improves the dynamic range of the optical radiation detector. If the transmission characteristics of the optical bandpass filter allow for the passing of only one significant band of radiation which is absorbed by the hydrogen peroxide vapor, the measured absorbance approaches the true absorbance of the hydrogen peroxide vapor at that wavelength. One preferred embodiment of operation as a single beam ultraviolet spectrophotometer with interference filter comprises use of the low pressure mercury light as the ultraviolet light source, a current regulating lamp driver, an optical bandpass filter selective for the 254 nm wavelength (the primary line for the low pressure mercury lamp), a thermally stabilized detector housing, and a thermally stabilized lamp housing. An even more preferred embodiment of the operation as a single beam ultraviolet spectrophotometer with interference filter comprises the use of the deuterium lamp as the ultraviolet light source, a current regulating lamp driver, a bandpass filter selective of a narrow band of wavelengths centered at 206 nm, a thermally stabilized detector housing, and a thermally stabilized lamp housing.

By using the deuterium lamp with a optical bandpass filter selective of 206 nm light, the diffuse output band of the deuterium lamp can be narrowed into a select band of wavelengths, thus minimizing deviations from Beer's law. Because the low pressure mercury lamp has such a strong principal emission peak at 254 nm, the improvement by adding an optical bandpass filter to the low pressure mercury lamp is less than for use of the deuterium lamp. The use of the deuterium lamp with an optical bypass filter selective of light centered at 206 nm is therefore the most preferred embodiment for a single beam ultraviolet spectrophotometer with interference filter.

Adding an optical bandpass filter while operating in the embodiment of single beam ultraviolet spectrometer with interference filter reduces the amount of light transmitted. The lower light level when using an optical bypass filter requires the use of high detector gains, which reduces the temperature stability and increases system noise. The embodiment of a single beam ultraviolet spectrometer with a low pressure mercury vapor lamp is therefore normally preferred over the embodiment of a single beam ultraviolet spectrometer with interference filter with a deuterium lamp, even though both are preferred embodiments.

Another embodiment of the present invention comprises the use of a single optical path containing hydrogen peroxide vapor on which the absorbance measurement is to be made and the use of two or more optical radiation detectors fitted with optical bandpass filters. This embodiment may be referred to as the single beam and dual wavelength ultraviolet spectrophotometer. At least one of the optical radiation detectors is fitted with an optical bandpass filter or other means of selecting a particular wavelength that is absorbed by the hydrogen peroxide vapor present in the sterilization chamber. A second optical radiation detector is fitted with an optical bandpass filter or other means of selecting a wavelength that is not absorbed by the hydrogen peroxide vapor or water vapor in the sterilization chamber. Because the output of the second optical radiation detector is independent of the hydrogen peroxide vapor, variations in the output from the second optical radiation detector represent changes in the optical measurement system. This might include instabilities in the light source or changes in the efficiency of the optical radiation detector. The output of the optical radiation detector that is selective to hydrogen peroxide vapor is divided by the output of the detector that is not selective to hydrogen peroxide vapor, providing an absorbance reading independent of variation in light source intensity.

Another embodiment comprises two optical radiation detectors selective to hydrogen peroxide vapor and two optical paths. The first optical path and detector are in fluid connection to a sterilization chamber where the amount of injected hydrogen peroxide vapor is to be measured and the second optical path and detector is not in fluid contact with hydrogen peroxide vapor injected into the sterilization chamber. This second optical path may contain a reference amount of hydrogen peroxide vapor or simply be clear of any varying concentrations of absorbing gasses. Output of the optical radiation detector in fluid connection with the sterilization chamber is divided by the output of the detector and optical path not in fluid contact with the sterilization chamber, providing an absorbance reading independent of variation in light source intensity.

Alternately, this embodiment can include just one radiation detector selective to hydrogen peroxide vapor and a mechanism to alternately select light from the first optical path and the second optical path to send to the single optical radiation detector. In this embodiment, the output of the single optical radiation detector alternates between the two optical paths. Since the output of the detector is changing in time, the signal needs to be stored and averaged in synchronism with the changing optical paths. Output of the optical radiation detector in synchronism with the first optical path is divided by the output of the optical radiation detector in synchronism with the second optical path leaving a result that is again independent of variations in the light source intensity. This type of sampled integration is well known by individuals versed in the art.

A variation on this approach would include the use of optical band pass filters selective to hydrogen peroxide for the reasons stated earlier.

The following example describes a typical procedure for performing an analysis of the concentration of hydrogen peroxide vapor.

EXAMPLE 1

Procedure for Performing a Hydrogen Peroxide Vapor Analysis

1. Pump down
2. RF or no RF (depends on whether or not the load requires warming, or if you want absolute values (i.e. a true zero baseline))
3. Vent
4. Pump down
5. Read first baseline.
6. Wait for 30 seconds read second baseline. Look for outgassing.
7. If stable, perform injection.

In all of the embodiments, a typical procedure for performing a hydrogen peroxide analysis is as follows. The optical path or the entire sterilization chamber is evacuated to a pressure of 500 millitorr or less to remove any hydrogen peroxide vapor or other absorbing gases to a level defined by the pressure, volume and temperature of the chamber. For reduction of hydrogen peroxide below the amount potentially present at 500 millitorr, radio frequency plasma may be energized for a period of several minutes to disassociate any remaining hydrogen peroxide. At this point the level of any remaining hydrogen peroxide will be below the resolution of the measurement system.

Dependent on the particular sterilization cycle, at this point the chamber may be vented to atmosphere and evacuated again to a level of 500 millitorr or one may proceed directly to injection of hydrogen peroxide.

Prior to injection, the system is maintained at 500 millitorr. A baseline reference is obtained and a dynamic check for any interfering gasses is performed. The first baseline is related to any initial absorbing hydrogen peroxide or interfering gasses in the sample. This is done such that signals generated after injections are related to the concentration of injected peroxide and not to initial absorbing hydrogen peroxide or interfering gases. After 15 to 30 seconds, a second baseline is recorded and compared to the first. If the two baselines differ by more than a small amount, the load to be sterilized is releasing hydrogen peroxide or an interfering gas into vapor, and the system is declared unstable.

At this point the chamber may be evacuated again, and the RF plasma may be run again. The process is repeated until the system reaches a stable baseline.

Hydrogen peroxide is then introduced through the liquid or vapor sterilant inlet port 44, and the absorbance in the optical path 40 is measured. The hydrogen peroxide can be introduced as a pure material or in a carrier gas such as air, nitrogen, argon, or other suitable carrier gas. Air is normally preferred. Heat or ultrasound may be used to help vaporize the hydrogen peroxide. The measured absorbance is compared to a calibration curve of absorbance versus hydrogen peroxide vapor concentration to obtain the concentration of hydrogen peroxide vapor in the optical path.

The calibration curve of hydrogen peroxide vapor concentration versus absorbance can be obtained in many different ways. One preferred method is as follows. All of the equipment to be sterilized is preferably removed from the sterilization chamber, and the sterilization chamber is evacuated to a low pressure, typically 500 millitorr or less. A measured amount of hydrogen peroxide is introduced into the sterilization chamber, and the pressure in the chamber is monitored as a finction of time. If the pressure changes, there is something in the chamber which is catalyzing the decomposition of hydrogen peroxide, or there is a leak in the system. Any remaining equipment is removed from the sterilization chamber, or the system is evacuated for a longer period of time to remove whatever is catalyzing the decomposition of the hydrogen peroxide. The process is repeated until the pressure in the system does not change after the hydrogen peroxide is introduced into the sterilization chamber. At this point, hydrogen peroxide samples can be weighed and introduced into the sterilization chamber via the liquid or vapor sterilant inlet port 44 to obtain a calibration curve. The volume of the sterilization chamber is known or can be measured using methods known to those skilled in the art. The concentration of hydrogen peroxide vapor in the chamber can then be calculated from the known weight of hydrogen peroxide and the known volume of the sterilization chamber.

The absorbance of this known concentration of hydrogen peroxide vapor is measured with the system of the present invention. The process is repeated with different weighed quantities of hydrogen peroxide to obtain a calibration curve of absorbance versus hydrogen peroxide concentration. This calibration curve is used to obtain the concentration of hydrogen peroxide vapor in the sterilization chamber from the absorbance measurement according to the method of the present invention. Other calibration methods can be used within the embodiment of this invention.

This procedure is dependent on the total mass of injected peroxide existing in a vaporous state. This condition will be met if the amount of injected peroxide and water is below that required for condensation of the peroxide. The exact value where condensation will occur is dependent on the percent concentration of the peroxide/water mix and the temperature in the sterilization chamber.

Figure 15:
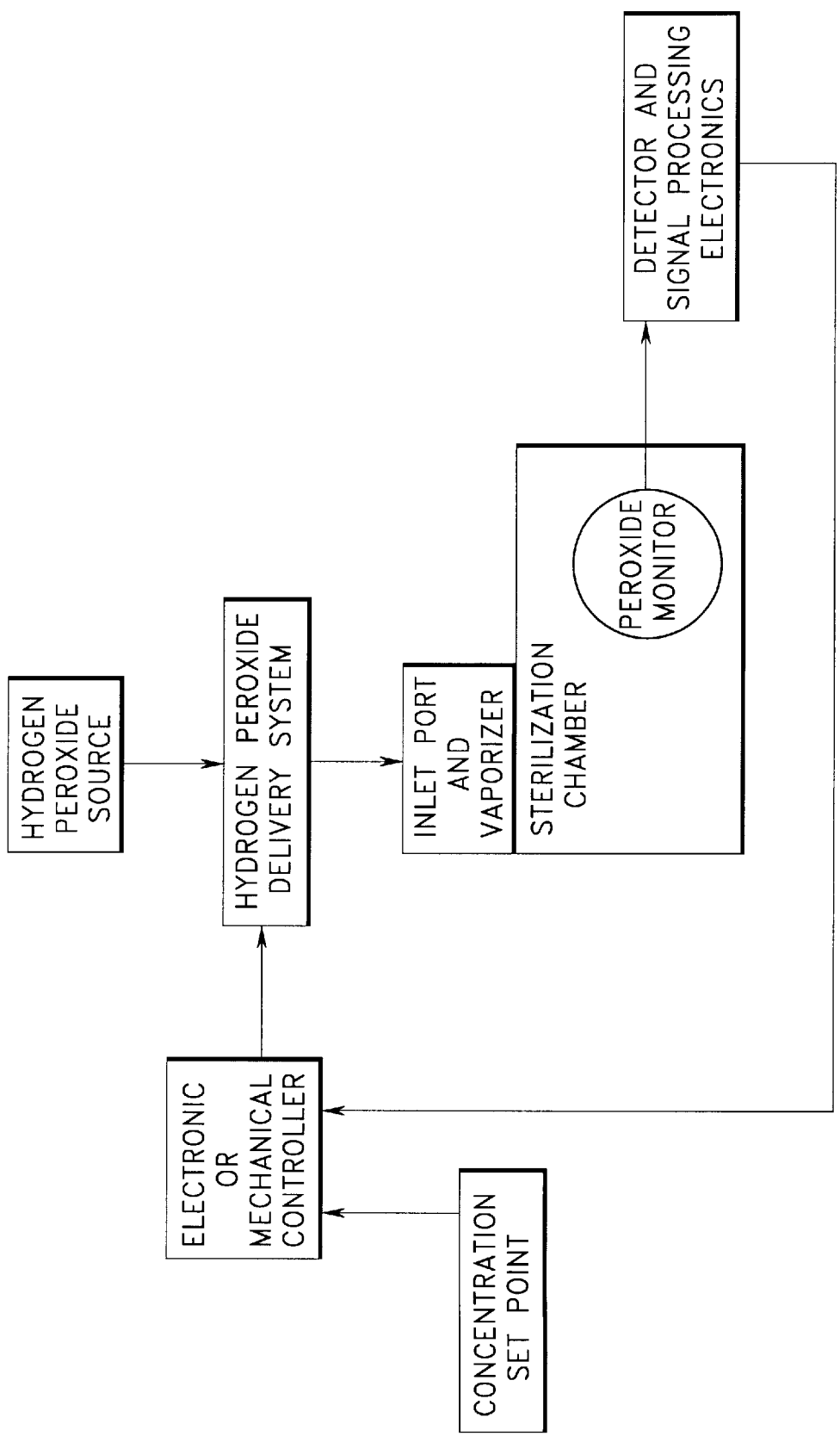
FIG. 15 is a schematic diagram of a feedback loop system for maintaining a certain concentration of hydrogen peroxide vapor in the sterilization chamber.

FIG. 15 shows a block diagram for the feedback loop used to control the concentration of hydrogen peroxide vapor or gas in the sterilization chamber.

The measurement system is used to determine the concentration of hydrogen peroxide within the sterilization chamber. An electrical signal representing the concentration is output from the detector and signal processing electronics. This value is fed back to an electrical or mechanical controller. The controller also has input corresponding to the desired concentration within the sterilization chamber. Based on these two signals and any other information the controller may have regarding the sterilization chamber, or the items undergoing sterilization, a determination is made of how much additional hydrogen peroxide to inject into the liquid or vapor sterilant inlet port.

The controller may implement a proportional, integral and derivative style function to determine the exact rate at which to inject hydrogen peroxide without exceeding a particular threshold. This function is commonly referred to as a PID and is well understood by one versed in the art. Alternatively, the controller may simply dispense hydrogen peroxide at a fixed rate, stopping only when the desired level within the sterilization chamber is exceeded.

The controller may consist of a microprocessor based electrical device and/or analog electrical circuitry that is capable of performing the necessary computations required for determining the amount of additional hydrogen peroxide to input to the sterilization chamber. The controller must also signal the delivery system to release an additional amount of hydrogen peroxide to the sterilization chamber. This process is repeated until the set point concentration is reached. At this point, the controller stops the release of hydrogen peroxide.

The following example demonstrates the use of the movable gas cell in mapping the concentration of hydrogen peroxide vapor throughout the sterilization chamber.

EXAMPLE 2

Use of Movable Gas Cell to Map Hydrogen Peroxide Vapor Concentration in a Sterilization Chamber The movable gas cell is placed in the sterilization chamber, hydrogen peroxide is introduced into the sterilization chamber through the liquid or vapor sterilant inlet port 44, and the concentration of hydrogen peroxide is measured using the movable gas cell and the method of the present invention. The movable gas cell is moved to another part of the sterilization chamber, and the same amount of hydrogen peroxide is introduced into the sterilization chamber under the same conditions. The concentration of hydrogen peroxide vapor is measured in the new location of the movable gas cell. The process is repeated, moving the movable gas cell throughout the sterilization chamber until a total of six or more measurements are done. The concentration distribution of the hydrogen peroxide vapor is plotted in three dimensions using contour plots to map the distribution of hydrogen peroxide vapor throughout the sterilization chamber.

The following example shows how the movable gas cell can be used to measure the concentration of hydrogen peroxide vapor in trays, containers, lumens, etc.

EXAMPLE 3

Determination of Hydrogen Peroxide Vapor Concentration in Trays. Containers. Lumens. etc. Using the Movable Gas Cell A mixture of trays, containers, lumens, and other devices is placed in the sterilization chamber. The movable gas cell is placed in one of the devices in the sterilization chamber, hydrogen peroxide is injected into the chamber through the liquid or vapor sterilant inlet port, and the concentration of hydrogen peroxide vapor is measured, using the movable gas cell and the method of the present invention. The movable gas cell is placed in a second device, hydrogen peroxide is injected, and the concentration of hydrogen peroxide vapor in the second device is measured using the method of the present invention. The movable gas cell is moved again into another device, and the process is repeated until the concentration of hydrogen peroxide vapor in all of the devices in the sterilization chamber has been measured.

The following example demonstrates the use of the method of the present invention in determining the rates of vaporization and diffusion of hydrogen peroxide.

EXAMPLE 4

Determination of Speed of Vaporization of Hydrogen Peroxide

Hydrogen peroxide is injected into a sterilization chamber which is equipped with an optical path with a single beam ultraviolet spectrophotometer with a low pressure mercury lamp. The hydrogen peroxide is injected at a single time through the liquid or vapor sterilant inlet port. The concentration of hydrogen peroxide vapor in the optical path is monitored as a function of time in order to determine the speed of vaporization of the hydrogen peroxide and the rate of diffusion of the hydrogen peroxide vapor.

The next example demonstrates the use of the movable gas cell in determining the speed of vaporization of hydrogen peroxide.

EXAMPLE 5

Determination of Speed of Vaporization Using Movable Gas Cell

The test of Example 4 is repeated, except that the movable gas cell is used rather than the fixed single beam ultraviolet spectrophotometer. The movable gas cell is moved to various locations in the sterilization chamber to determine the relative rates of diffusion of hydrogen peroxide vapor throughout the sterilization chamber.

The next example demonstrates the use of both the single beam ultraviolet spectrophotometer and the movable gas cell in measuring the effects of loading.

EXAMPLE 6

Determination of Effects of Amount and Configuration of Loading

Tests are performed on the rates of vaporization and diffusion of hydrogen peroxide vapor in the sterilization chamber as a function of the amount of equipment to be sterilized and the arrangement of the equipment in the sterilization chamber. Both the fixed single beam ultraviolet spectrophotometer and the movable gas cell are used in these tests.

The following example illustrates the use of the method of the present invention to determine the effect of the temperature of the equipment loaded into the sterilization chamber.

EXAMPLE 7

Determination of Effects of Temperature of the Equipment

Tests are performed as in Example 6, except that the temperature of the equipment which is loaded into the sterilization chamber is varied. In this manner, the effect of the temperature of the equipment on the distribution of hydrogen peroxide vapor is determined.

The next example demonstrates the use of the movable gas cell in closed loop control.

EXAMPLE 8

Use of Movable Gas Cell for Closed Loop Control

The movable gas cell is used as in Example 2 to determine the location in the sterilization chamber having the lowest concentration of hydrogen peroxide vapor. The movable gas cell is placed in the location of the lowest concentration, and the movable gas cell is used as a sensing device to measure the concentration of hydrogen peroxide in the sterilization chamber. This lowest concentration is fed back to an electrical or mechanical controller that compares the measured concentration with that of the desired set point concentration. Based on these two signals and any other information the controller may have regarding the sterilization chamber or the items undergoing sterilization, a determination is made of how much additional hydrogen peroxide to inject into the liquid or vapor sterilant inlet port. When the set point concentration is reached, the controller stops the release of hydrogen peroxide. In this manner, closed loop control of hydrogen peroxide vapor concentration is established, using the movable gas cell as a monitoring device to regulate the hydrogen peroxide concentration at a unique location.

What is claimed is:

1. A method of determining the concentration of hydrogen peroxide vapor or hydrogen peroxide gas in a contained area comprising:
    (a) evacuating said contained area to a pressure between 0 and 10 torr;
    (b) exposing said contained area to plasma so as to remove species in said contained area that would interfere with measurement of said hydrogen peroxide vapor or hydrogen peroxide gas;
    (c) establishing a baseline absorbance in said contained area at a wavelength between 200 and 400 nanometers after step (b);
    (d) introducing hydrogen peroxide into said contained area to form a sample, wherein said introducing occurs after step (c);
    (e) measuring the absorbance of said sample at a wavelength between 200 and 400 nanometers; and
    (f) determining the concentration of hydrogen peroxide vapor or hydrogen peroxide gas in said sample from said absorbance measured in steps (c) and (e).

2. The method of claim 1, additionally comprising adjusting said concentration of hydrogen peroxide after step (F).

3. The method of claim 1, wherein said concentration of hydrogen peroxide vapor or hydrogen peroxide gas is compared with a desired set point concentration of hydrogen peroxide and wherein hydrogen peroxide is incrementally added to said contained area so as to increase said concentration of hydrogen peroxide in said contained area until said set point concentration is reached.

4. The method of claim 1, wherein said absorbance is measured at a wavelength of 254 nanometers.

5. The method of claim 1, wherein said absorbance is measured with a mercury lamp.

6. The method of claim 4, wherein said mercury lamp is current regulated.

7. The method of claim 1, wherein said absorbance is measured at a wavelength of 206 nanometers.

8. The method of claim 1, wherein said absorbance is measured with a deuterium lamp.

9. The method of claim 1, wherein the concentration of hydrogen peroxide vapor or hydrogen peroxide gas in said sample is determined from said absorbance using Beer's law.

10. The method of claim 1, wherein the concentration of hydrogen peroxide vapor or hydrogen peroxide gas in said sample is determined by comparing said absorbance with a calibration curve of absorbance versus the concentration of hydrogen peroxide vapor or hydrogen peroxide gas.

11. The method of claim 1, further comprising terminating said exposing before or during said introducing.

12. The method of claim 1, wherein said absorbance is measured with a peroxide monitor which is movable in said contained area.

13. The method of claim 1, wherein said absorbance is measured with a peroxide monitor which is fixed in position.

14. The method of claim 1, further comprising repeating one or more steps at least one time.

15. The method of claim 1, further comprising exposing said contained area to plasma, wherein said exposing occurs after said determining.

16. The method of claim 1, further comprising establishing a second baseline absorbance and comparing said second baseline absorbance with said baseline absorbance.

17. The method of claim 1, further comprising repeating said evacuating and/or said exposing.

18. The method of claim 1, further comprising determining no interfering gases are present.

19. The method of claim 1, further comprising heating a load in said contained area during said exposing.

20. The method of claim 1, further comprising adjusting said concentration of hydrogen peroxide vapor or hydrogen peroxide gas in said contained area.

21. The method of claim 1, further comprising sterilizing a load in said contained area.

* * * * *